US012728184B2

(12) United States Patent
Maxwell et al.

(10) Patent No.: US 12,728,184 B2
(45) Date of Patent: Sep. 8, 2026

(54) TISSUE-MIMICKING HYDROGEL MATERIAL

(71) Applicant: University of Washington, Seattle, WA (US)

(72) Inventors: Adam D. Maxwell, Seattle, WA (US); Yashwanth Nanda Kumar, Seattle, WA (US)

(73) Assignee: University of Washington, Seattle, WA (US)

( * ) Notice: Subject to any disclaimer, the term of this patent is extended or adjusted under 35 U.S.C. 154(b) by 445 days.

(21) Appl. No.: 18/297,799

(22) Filed: Apr. 10, 2023

(65) Prior Publication Data

US 2023/0321327 A1 Oct. 12, 2023

Related U.S. Application Data

(60) Provisional application No. 63/330,155, filed on Apr. 12, 2022.

(51) Int. Cl.
*A61L 31/04* (2006.01)
*A61B 8/00* (2006.01)
(Continued)

(52) U.S. Cl.
CPC ........... *A61L 31/041* (2013.01); *A61L 31/145* (2013.01); *A61B 8/58* (2013.01); *G01H 3/005* (2013.01);
(Continued)

(58) Field of Classification Search
CPC ................ A61L 31/041; A61L 31/145; G01N 2291/2694; G01N 2291/02854; G01N 29/30; G01H 3/005; A61B 8/58
(Continued)

(56) References Cited

U.S. PATENT DOCUMENTS 4,002,173 A * 1/1977 Manning ............. C08B 37/0018 514/59
4,124,638 A * 11/1978 Hansen ................. C08F 220/56 564/204
(Continued)

FOREIGN PATENT DOCUMENTS

CA 1285902 C * 7/1991
CN 118360124 A * 7/2024 ............ C12M 23/16
(Continued)

OTHER PUBLICATIONS

Dong et al., A Pattern Designable Hydrogel Vessel Phantom for Ultrasound Imaging, 2019 IEEE International Ultrasonics Symposium (IUS), Glasgow, Scotland, Oct. 6-9, 2019, pp. 579-582 (Year: 2019).*

(Continued)

*Primary Examiner* — Stephanie E Bloss
*Assistant Examiner* — Kevin C Butler
(74) *Attorney, Agent, or Firm* — CHRISTENSEN O'CONNOR JOHNSON KINDNESS PLLC

(57) ABSTRACT

A phantom for fibrous tissue, the phantom formed from a precursor solution including about 30-90 wt % of water, acrylamide, and alginate, where the acrylamide and alginate, in combination, are about 10 to 70 wt % of the precursor solution, and where a ratio of acrylamide to alginate is in the range of about 60:40 to about 99:1 w/w.

20 Claims, 11 Drawing Sheets
(8 of 11 Drawing Sheet(s) Filed in Color)

(51) Int. Cl.
*A61L 31/14* (2006.01)
*G01H 3/00* (2006.01)
*G01N 29/30* (2006.01)

(52) U.S. Cl.
CPC ... *G01N 29/30* (2013.01); *G01N 2291/02854* (2013.01); *G01N 2291/2694* (2013.01)

(58) Field of Classification Search
USPC .......................................................... 73/1.86
See application file for complete search history.

(56) References Cited

U.S. PATENT DOCUMENTS

| | | | | |
|---|---|---|---|---|
| 5,283,196 | A * | 2/1994 | Hochstrasser | C08F 220/56 436/178 |
| 7,159,847 | B2 * | 1/2007 | Schroeder | F16K 31/084 251/359 |
| 8,016,757 | B2 * | 9/2011 | Kaczkowski | A61B 8/5223 601/3 |
| 8,282,800 | B2 * | 10/2012 | Rowell | B01D 57/02 204/468 |
| 9,345,790 | B2 * | 5/2016 | Frank | A61N 5/1007 |
| 2004/0140215 | A1 * | 7/2004 | Panattoni | C07K 1/26 204/620 |
| 2010/0051462 | A1 * | 3/2010 | Rowell | B01D 57/02 204/469 |
| 2019/0053790 | A1 * | 2/2019 | Grover | A61L 27/443 |
| 2023/0321327 | A1 * | 10/2023 | Maxwell | A61L 31/145 424/423 |
| 2024/0139552 | A1 * | 5/2024 | Duryea | A61B 34/30 |

FOREIGN PATENT DOCUMENTS

| | | | | |
|---|---|---|---|---|
| CN | 119455104 | A * | 2/2025 | A61L 27/52 |
| DE | 112009000374 | T5 * | 1/2011 | A61B 17/00 |
| EP | 169397 | A * | 1/1986 | B01D 57/02 |
| EP | 0159694 | B1 * | 1/1992 | G01N 27/44704 |
| JP | H0699377 | B2 * | 12/1994 | C07C 233/38 |
| WO | WO-03079805 | A1 * | 10/2003 | C12P 21/02 |
| WO | WO-2009091113 | A1 * | 7/2009 | G01N 33/6803 |
| WO | WO-2009103220 | A1 * | 8/2009 | G09B 23/286 |
| WO | WO-2012028683 | A1 * | 3/2012 | A61K 39/39591 |

OTHER PUBLICATIONS

Bush, N.L., et al., "Gelatine-alginate complex gel: A new acoustically tissue-equivalent material," Ultrasound in Med & Biol. 9(5), pp. 479-484, 1983 (Year: 1983).*

Wei et al., Histotripsy Beyond the Intrinsic Cavitation Threshold Using Very Short Ultrasound Pulses: Microtripsy, IEEE Transactions on Ultrasonics, Ferroelectrics, and Frequency Control, vol. 61, No. 2, Feb. 2014, pp. 251-265 (Year: 2014).*

Wang, T.Y., et al., "Imaging feedback of histotripsy treatments using ultrasound shear wave elastography," IEEE Trans Ultrason Ferroelectr Freq Control 2012;59: pp. 1167-1181 (Year: 2012).*

Kumar et al., Development of Tough Hydrogel Phantoms to Mimic Fibrous Tissue for Focused Ultrasound Therapies, Ultrasound in Med. & Biol., vol. 48, No. 9, pp. 17621777, 2022 (Year: 2022).*

Peek, A.T., et al., "Robust and Durable Aberrative and Absorptive Phantom for Therapeutic Ultrasound Applications," The Journal of the Acoustical Society of America, 151(5), 3007, May 4, 2022 (Year: 2022).*

Dabbagh, A., et al., "Reusable Heat-Sensitive Phantom for Precise Estimation of Thermal Profile in Hyperthermia Application," International Journal of Hyperthermia, 30(1), 2014, p. 66-74 (Year: 2014).*

Fitzgerald et al., Tunable Stress Relaxation Behavior of an Alginate-Polyacrylamide Hydrogel: Comparison with Muscle Tissue, ACS Publications, American Chemical Society, 2015, pp. 1497-1505 (Year: 2015).*

Tatarinov, A., et al., "Modeling the influence of mineral content and porosity on ultrasound parameters in bone by using synthetic phantoms." Mech Compos Materials, vol. 35(2): pp. 147-154, 1999 (Year: 1999).*

Worthington, A.E., et al., "Ultrasound properties of human prostate tissue during heating," Ultrasound Med Biol. 2002;28: pp. 1311-1318 (Year: 2002).*

Yang et al., Strengthening Alginate/Polyacrylamide Hydrogels Using Various Multivalent Cations, ACS Publications, American Chemical Society, 2013, pp. 10418-10422 (Year: 2013).*

Zell et al., Acoustical properties of selected tissue phantom materials for ultrasound imaging, Physics in Medicine and Biology, 52 (2007) N475-N484 (Year: 2007).*

Stewart, E.A., et al., "Uterine fibroids," Nature Reviews Disease Primers 2016, vol. 2, 18 pages.

Sun, J.Y., et al., "Highly stretchable and tough hydrogels," Nature Publishing Group, 489: pp. 133-136, Sep. 6, 2012.

Tatarinov, A., et al., "Modeling the influence of mineral content and porosity on ultrasound parameters in bone by using synthetic phantoms." Mech Compos Materials, vol. 35(2): pp. 147-154, 1999.

Maisavljevich, E., et al., "Effects of f-number on the histotripsy intrinsic threshold and cavitation bubble cloud behavior," Phys Med Biol IOP Publishing, 2017;62: pp. 1269-1290.

Maisavljevich, E., et al., "Effects of tissue mechanical properties on susceptibility to histotripsy-induced tissue damage," Phys Med Biol Institute of Physics Publishing, 2014;59: pp. 253-270.

Wang, T.Y., et al., "Imaging feedback of histotripsy treatments using ultrasound shear wave elastography," IEEE Trans Ultrason Ferroelectr Freq Control 2012;59: pp. 1167-1181.

Wang, T.Y., et al., "An Efficient Treatment Strategy for Histotripsy by Removing Cavitation Memory," Ultrasound Med Biol 2012;38: pp. 753-766.

Wang, Y.N., et al., "Mechanical Decellularization of Tissue Volumes Using Boiling Histotripsy," Phys. Med. Biol. NIH Public Access, 2019; 63(23): 235023, 20 pages.

Wells, R.G., et al., "Tissue Mechanics and Fibrosis," Biochim Biophys Acta. NIH Public Access, Jul. 2013, 1832(7): pp. 884-890.

Wilson, C.T., et al., "Comparative study of the dynamics of laser and acoustically generated bubbles in viscoelastic media," Physical Review E 99 (2019), 10 pages.

Worthington, A.E., et al., "Ultrasound properties of human prostate tissue during heating," Ultrasound Med Biol. 2002;28: pp. 1311-1318.

Yang, C.H., et al., "Strengthening alginate/polyacrylamide hydrogels using various multivalent cations," ACS Appl Mater Interfaces 2013;5: pp. 10418-10422.

Yang, S., et al., "High-intensity focused ultrasound ablation: An in vitro agarose gel model," Int Journal Clin Exp Med. 2017;10(11): pp. 15302-15308.

Zell, K., et al., "Acoustical properties of selected tissue phantom materials for ultrasound imaging," Phys Med Biol. 2007;52, 11 pages.

Zhang, J., et al., "Animal models of benign prostatic hyperplasia," Prostate Cancer and Prostatic Diseases 2021;24:49-57.

Discher, D.E., et al., "Growth factors, matrices, and forces combine and control stem cells," Science NIH Public Access, 2009;324:1673.

Dabbagh, A., et al., "Reusable Heat-Sensitive Phantom for Precise Estimation of Thermal Profile in Hyperthermia Application," International Journal of Hyperthermia, 30(1), 2014, p. 66-74.

Lindner, U., et al., "Construction and Evaluation of an Anatomically Correct Multi-Image Modality Compatible Phantom for Prostate Cancer Focal Ablation," The Journal of Urology, 184(1), Jul. 2010, p. 352-357.

Dong, F. et al., "A Pattern Designable Hydrogel Vessel Phantom for Ultrasound Imaging," IEEE, Oct. 6-9, 2019.

Peek, A.T., et al., "Robust and Durable Aberrative and Absorptive Phantom for Therapeutic Ultrasound Applications," The Journal of the Acoustical Society of America, 151(5), 3007, May 4, 2022.

Peek, A.T., et al., "Bilayer Aberration-Inducing Gel Phantom for High Intensity Focused Ultrasound Applications.," The Journal of the Acoustical Society of America, vol. 148(6), 3569, Dec. 10, 2020.

(56) References Cited

OTHER PUBLICATIONS

Sun, M.K., et al., "Reusable Tissue-Mimicking Hydrogel Phantoms for Focused Ultrasound Ablation," Ultrasonics Sonochemistry, 23, Mar. 2015, pp. 399-405.
Dabbagh, A., et al., "Tissue-Mimicking Gel Phantoms for Thermal Therapy Studies." Ultrasonic Imaging, 2014; 36(4): 291-316.
Kumar, Y.N. et al., "Development of Tough Hydrogel Phantoms to Mimic Fibrous Tissue for Focused Ultrasound Therapies." Ultrasound in Medicine & Biology, 48(9), Sep. 2022, pp. 1762-1777.
Kumar, Y.N. et al., "Bubble cloud progression in fibrous tissue mimicking hydrogels at different histotripsy sonications," J Acoust Soc Am., 150, A29 (2021).
Bercoff, J., et al., "A new real time imaging mode for assessing quantitatively soft tissue viscoelasticity," Proc—IEEE Ultrason Symp 2008, 4 pages.
Bt Ibrahim, S.F., et al., "Sodium alginate film: the effect of crosslinker on physical and mechanical properties," 2019 IOP Conf Series: Materials Science and Engineering 509.
Bush, N.L., et al., "Gelatine-alginate complex gel: A new acoustically tissue-equivalent material," Ultrasound in Med & Biol. 9(5), pp. 479-484, 1983.
Cabrelli, L.C., et al., "Acoustic and Elastic Properties of Glycerol in Oil-Based Gel Phantoms," Ultrasound in Med & Biol. 43(9), pp. 2086-2094, 2017.
Choi, M.J., et al., "A Tissue Mimicking Polyacrylamide Hydrogel Phantom for Visualizing Thermal Lesions Generated by High Intensity Focused Ultrasound," Ultrasound in Med & Biol. 39(3), pp. 439-448, 2013.
Clarke, A.J., et al., "A phantom for quantitative ultrasound of trabecular bone," Phys Med Biol. 1994;39, 12 pages.
Culjat, M.O., et al., "A review of tissue substitutes for ultrasound imaging," Ultrasound in Med & Biol. 36(6), pp. 861-873, 2010.
Dunmire, B., et al., "Characterizing an Agar/Gelatin phantom for image guided dosing and feedback control of high-intensity focused ultrasound," Ultrasound in Med & Biol. 39(2), pp. 300-311, 2013.
Duryea, A., et al., "Removal of residual nuclei following a cavitation event using low-amplitude ultrasound," IEEE Trans Ultrason Ferroelectr Freq Control 61(10), pp. 1619-1626, 2014.
Geoghegan, R., et al., "A Tissue-Mimicking Prostate Phantom for 980nm Laser Interstitial Thermal Therapy." Int J Hyperthermia NIH Public Access 2019, 36(1), pp. 993-1002.
Gong, J.P., et al., "Double-network hydrogels with extremely high mechanical strength.," Adv Mater 2003, 15(14), pp. 1155-1158.
Guan, Y., et al., "Histotripsy Produced by Hundred-Microsecond-Long Focused Ultrasonic Pulses: A Preliminary Study," Ultrasound in Med & Biol. 42(9), pp. 2232-2244, 2016.
Guntur, S.R., et al., "An Improved Tissue-Mimicking Polyacrylamide Hydrogel Phantom for Visualizing Thermal Lesions with High-Intensity Focused Ultrasound," Ultrasound in Med & Biol. 40(11), pp. 2680-2691, 2014.
Hall, T.L., et al., "Histotripsy of the Prostate: Dose Effects in a Chronic Canine Model," Urology Elsevier Inc., 74(4), pp. 932-937, 2009.
Hempel, C.R., et al., "Histotripsy fractionation of prostate tissue: Local effects and systemic response in a canine model," J Urol 2011, 185(4), pp. 1484-1489.
Hendricks-Wenger, A., et al., "Histotripsy for the Treatment of Cholangiocarcinoma Liver Tumors: In Vivo Feasibility and Ex Vivo Dosimetry Study," IEEE Trans Ultrason Ferroelectr Freq Control 2021, 68(9):2953-2964.
Hori, R.Y., et al., "Mechanical properties of the fibrous tissue found at the bone-cement interface following total joint replacement," J Biomed Mater Res. 1982;16:911-927.
Ishigooka, M., et al., "Relative and total volume of histological components in benign prostatic hyperplasia: Relationships between histological components and clinical findings," The Prostate, 29, pp. 77-82, 1996.
Jianhai, Y., et al., "Strengthening Alginate/Polyacrylamide Hydrogels Using Various Multivalent Cations," ACS Applied Materials & Interfaces, Oct. 2013, 6 pages.
Kharine, A., et al., "Poly(vinyl alcohol) gels for use as tissue phantoms in photoacoustic mammography," Phys Med Biol 48, pp. 357-370, 2003.
Khokhlova, T.D., et al., "Dependence of Boiling Histotripsy Treatment Efficiency on HIFU Frequency and Focal Pressure Levels," Ultrasound in Med & Biol. 43(9), pp. 1975-1985, 2017.
Khokhlova, T.D., et al., "Effect of Stiffness of Large Extravascular Hematomas on Their Susceptibility to Boiling Histotripsy Liquefaction in Vitro," Ultrasound in Med & Biol. 46(8), pp. 2007-2016, 2020.
Kondo, T., et al., "New tissue mimicking materials for ultrasound phantoms," Proc—IEEE Ultrason Symp. 3, pp. 1664-1667, 2005.
Lin, K.W., et al., "Synthesis of monopolar ultrasound pulses for therapy: The frequency-compounding transducer," IEEE Trans Ultrason Ferroelectr Freq Control, 61(7):1123-1136, Jul. 2014.
Lin, K.W., et al., "Histotripsy beyond the intrinsic cavitation threshold using very short ultrasound pulses: Microtripsy," IEEE Trans Ultrason Ferroelectr Freq Control, 61(2): 251-265, Feb. 2014.
Madsen, E.L., et al., "Liquid or solid ultrasonically tissue-mimicking materials with very low scatter," Ultrasound in Med & Biol. 24(4): pp. 535-542, 1998.
Mancia, L., et al., "Predicting Tissue Susceptibility to Mechanical Cavitation Damage in Therapeutic Ultrasound," Ultrasound in Med & Biol. 43(7): pp. 1421-1440, 2017.
Mancia, L., et al., "Modeling tissue-selective cavitation damage," 2019 Phys Med Biol Institute of Physics Publishing 64, 31 pages.
Maxwell, A.D., et al., "Noninvasive ureterocele puncture using pulsed focused ultrasound: An in vitro study," J Endourol 28: pp. 342-346, 2014.
Maxwell, A.D., et al., "Cavitation clouds created by shock scattering from bubbles during histotripsy," J Acoust Soc Am 130(4): pp. 1888-1898, Oct. 2011.
Maxwell, A.D., et al., "A tissue phantom for visualization and measurement of ultrasound-induced cavitation damage," Ultrasound in Med & Biol. 36(12): pp. 2132-2143, 2010.
Moreland, R.B., et al., "Pathophysiology of Peyronie's disease," Int. J. Impot. Research 14: pp. 406-410, 2002.
Pogue, B.W., "Review of tissue simulating phantoms for optical spectroscopy, imaging and dosimetry," J Biomed Optics 11(4), 2006, 16 pages.
Roberts, W.W., et al., "Pulsed cavitational ultrasound: A noninvasive technology for controlled tissue ablation (histotripsy) in the rabbit kidney," J Urol vol. 175, pp. 734-738, Feb. 2006.
Roberts, W.W., et al., "Histotripsy of the prostate using a commercial system in a canine model," J Urol vol. 191, pp. 860-865, Mar. 2014.
Rodriguez-Nieves, A., et al., "Prostatic fibrosis, lower urinary tract symptoms, and BPH," Nat Rev Urol. 10(9), pp. 546-550, Sep. 2013.
Schade, G.R., et al., "Urethral-sparing histotripsy of the prostate in a canine model," Urology Elsevier Inc., 80(3): pp. 730-735, Sep. 2012.
Schade, G.R., et al., "Prostate histotripsy: Evaluation of prostatic urethral treatment parameters in a canine model," BJU Int. 113(3): pp. 498-503, Mar. 2014.
Schuppan, D., et al., "Liver cirrhosis," Lancet 371: pp. 838-851, Mar. 2008.
Schuster, T.G., et al., "Histotripsy Treatment of Benign Prostatic Enlargement Using the Vortx Rx System: Initial Human Safety and Efficacy Outcomes," Urology 114: pp. 184-187, 2018.
Shapiro, E., et al., "The relative proportion of stromal and epithelial hyperplasia is related to the development of symptomatic benign prostate hyperplasia," Journal of Urology, 147: pp. 1293-1297, May 1992.

* cited by examiner

Phase Contrast of 90/10 Acrylamide/Alginate Gel

Masson's Trichome of *Ex-Vivo* Human Prostate Tissue

Transducer of pulses:

3000 2000 1000 500 400

Transducer of pulses:

300 200 100 50 20

Transducer

TISSUE-MIMICKING HYDROGEL MATERIAL

CROSS-REFERENCES TO RELATED APPLICATIONS

This application claims the benefit of U.S. Provisional Application 63/330,155, filed Apr. 12, 2022, the entire disclosure of which is hereby incorporated by reference.

STATEMENT OF GOVERNMENT LICENSE RIGHTS

This invention was made with Government support under R01-DK119310 awarded by National Institutes of Health. The Government has certain rights in the invention.

BACKGROUND

Tissue mimicking phantoms are an important tool for the development, optimization, and performance testing of therapeutic ultrasound techniques. These phantoms provide a cost-effective medium for direct feedback on optimal treatment strategies in a low-risk environment before continuing to pre-clinical in-vivo models and clinical trials. Tissue phantoms have been characterized and utilized in approximating both soft (e.g., blood and liver) and hard (e.g., whole bone and dental) tissue for therapeutic ultrasound. Soft-tissue phantoms include agarose, gelatin, polyacrylamide, polyurethane and oil-based gels with hard tissue phantoms being epoxy or acrylic plastic, among others.

Though there is a broad variety of phantoms available for mimicking tissues with different stiffnesses suitable for evaluating thermal ultrasound therapies, there are few material substitutes which adequately represent fibrous tissue with high inherent toughness, a quality that may be especially important in mechanical cavitation-based ultrasound therapies. A typical stress-strain curve for a fibrous tissue is nonlinear with large deformations at lower loads, following which the material becomes stiffer at increasing loads and becomes linear at higher loads. Fibrous tissue in general is very compliant and undergoes large strains with load thus leading to an overall larger area under the stress-strain curve and greater total energy input to produce mechanical failure. Some hybrid gel phantoms like Polyacrylamide-alginate also possess a larger area under the stress strain curve and this attribute is referred to as inherent toughness or fracture toughness of the material.

Inherent toughness is found in many pathologic tissues, including benign prostatic hyperplasia (BPH), wherein the tissue can form fibromuscular (collagenous) components that toughen the tissue and play a role in producing BPH symptoms. Ultrasound techniques have been developed to treat BPH, such as histotripsy, which is a non-invasive therapy that uses short, high-pressure ultrasound pulses to mechanically fractionate tissue. Investigators found early success in treating in-vivo canine prostates using high pulse repetition frequencies (PRF), demonstrating histotripsy as a promising treatment modality for BPH. However, during a subsequent clinical trial, histotripsy did not produce objective improvements in clinical symptoms or changes in prostatic volume. A potential reason for the reduced efficacy is due to the differences in mechanical characteristics between non-BPH canine (as tested in the prior pre-clinical models) and human BPH tissue. In contrast to non-BPH canine prostate, tough fibromuscular stromal hyperplasia tends to predominate in human BPH making it more resistant to the effects of histotripsy. This reasoning is further supported by multiple prior studies which have shown that fibrous tissues are, in general, more resistant to histotripsy-induced tissue damage. These biological differences highlight the importance of having preclinical models (i.e., tissue phantoms and animal models) that adequately represent the target tissue.

The heterogeneous nature of prostatic tissue provides a unique challenge in creating an appropriate tissue phantom. Despite being considered a soft tissue, fibromuscular stromal hyperplasia (collagen remodeling) wherein fibrosis leads to an increase in elastic modulus due to collagen and elastin cross-linking leave the prostate resistant to the treatment effects of histotripsy. Traditionally, soft agarose, alginate and polyacrylamide gels have been used as tissue mimics for prostate. Although agarose gels can represent soft glandular elements of prostatic tissue; they have low toughness and tend to break down easily at low stresses, and existing literature suggests that the fracture toughness for polyacrylamide and alginate gels are small and do not capture the mechanical characteristics of average and tough BPH tissue. Additionally, the phantom must be optically transparent to visualize histotripsy cavitation on high-speed photography. Thus, an ideal phantom would be one that can approximate the mechanical and acoustic properties of fibrous tissues, is optically transparent, can be easily reformulated to approximate a range of tissue properties (e.g., soft, average, and tough BPH tissue with stiffnesses ranging from 15-100 kPa), responds to histotripsy in a similar manner to tissue in terms of the fracture mechanics and the nucleation and evolution of bubble clouds that cause the mechanical damage, allows histotripsy lesions to be easily detected (to measure lesion volume and size) and analyzed (in ability to cause complete ablation) for optimization of treatment parameters, and is relatively simple and inexpensive to prepare.

Such a phantom would be valuable not only for investigation of BPH, but also for other inherently tough, treatment resistant, diseased tissues, including uterine fibroids, fibrous tumors such as cholangiocarcinoma and pancreatic ductal adenocarcinoma, and plaques caused by Peyronie's disease or atherosclerosis. Like BPH, advancements in therapeutic ultrasound for these diseases will depend on identifying effective treatment strategies in accurate preclinical models.

Accordingly, phantoms with the characteristics described above are needed.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

Disclosed herein is a phantom for fibrous tissue, the phantom formed from a precursor solution. In some embodiments, the precursor solution includes about 30-90 wt % of water, acrylamide, and alginate, wherein the acrylamide and alginate, in combination, are about 10 to 70 wt % of the precursor solution, and wherein a ratio of acrylamide to alginate is in the range of about 60:40 to about 99:1 w/w.

In another aspect, a method of making the phantom for fibrous as described herein is disclosed. In some embodiments, the method includes providing about 30 to 90 wt % of water, adding sodium alginate to the water, adding acrylamide to the homogenous solution, where the sodium alginate and the acrylamide, in combination, are about 10 to 70 wt % of the precursor solution, and where the ratio between the acrylamide and the alginate is 60:40 to 99:1 w/w to form a precursor solution, stirring the precursor solution, degassing the precursor solution, curing the precursor solution to form a gel, and soaking the gel in a crosslinking solution.

In yet another aspect, a method of evaluating a treatment with phantom described herein is disclosed.

DESCRIPTION OF THE DRAWINGS

The patent or application file contains at least one drawing executed in color. Copies of this patent or patent application publication with color drawing(s) will be provided by the Office upon request and payment of the necessary fee. The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
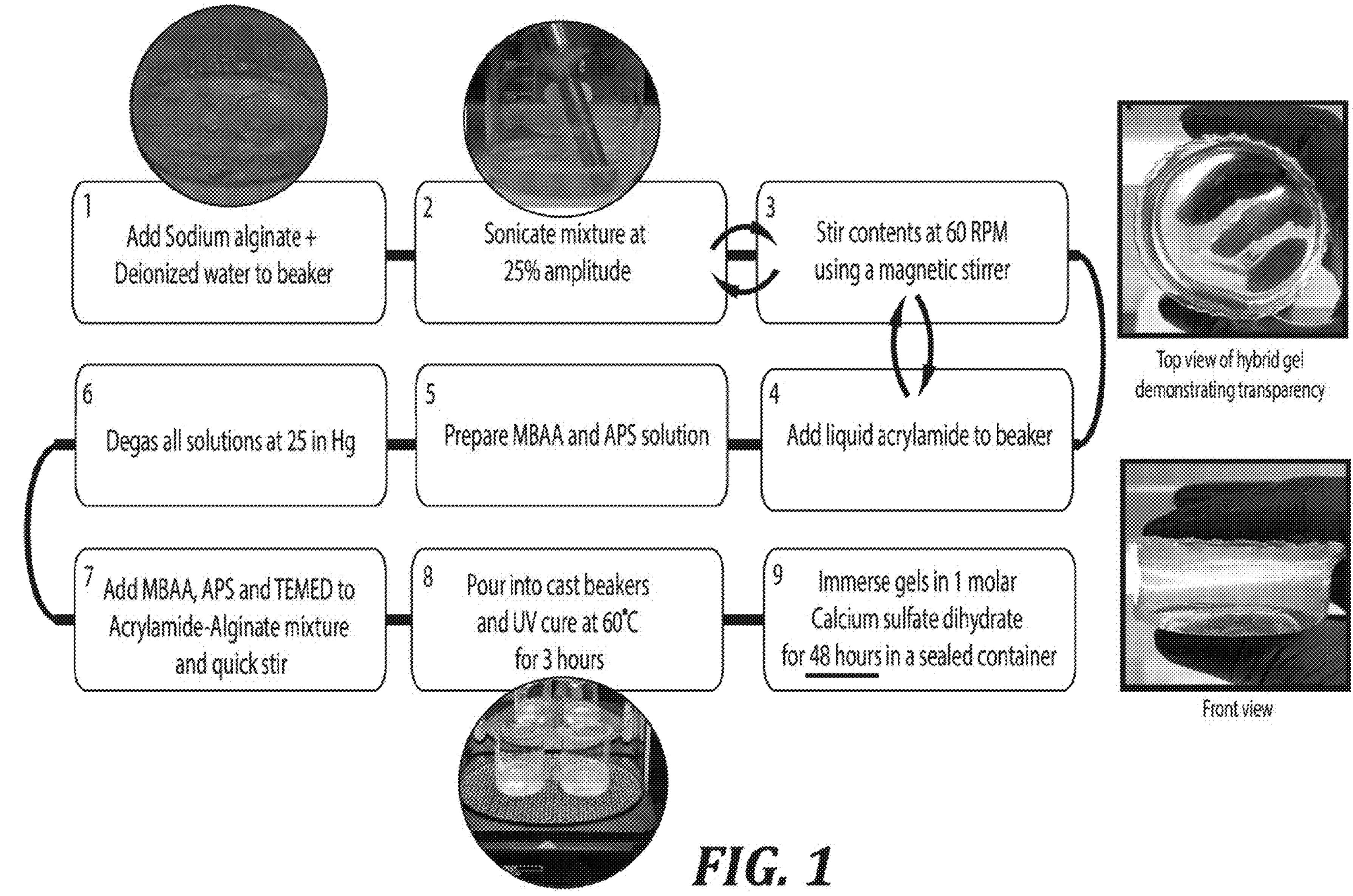
FIG. 1 is a method for preparing a phantom, in accordance with the present technology.

While illustrative embodiments have been illustrated and described, it will be appreciated that various changes can be made therein without departing from the spirit and scope of the disclosure.

Described herein is phantom for fibrous tissue, the phantom formed from a precursor solution including about 30-90 wt % of water, acrylamide, and alginate, where the acrylamide and alginate, in combination, are about 10 to 70 wt % of the precursor solution, and where a ratio of acrylamide to alginate is in the range of about 60:40 to about 99:1 w/w.

In some embodiments, the precursor solution further includes 0.10-0.30 wt % of ammonium persulphate (APS) based on the weight of acrylamide, 0.02-0.10 wt % N,N-methylenebisacrylamide (MBAA) based on the weight of acrylamide, and 0.10-0.50 wt % of N,N,N',N'-tetramethylethylenediamine (TEMED) based on the weight of acrylamide. In some embodiments, the ratio of acrylamide to alginate is in the range of about 80:20 to 95:5. In some embodiments, the precursor solution further includes calcium sulfate dihydrate.

In some embodiments, the stiffness of the phantom ranges from 5-1300 kPa. In some embodiments, the density of the phantom is 1000-1200 kg/m3. In some embodiments, the phantom is homogenous. In some embodiments, the fibrous tissue is selected from connective tissue, prostatic tissue, uterine fibroids, fibrous tumors, blood clots, vascular plaques, cirrhosis of the liver, cirrhosis tumors, organ scars and adhesions, cystic and abscess capsular tissue, skin, uterine fibroids, fibroadenomas, scar tissue, or ureteral structures. In some embodiments, the phantom is optically transparent. In some embodiments, the phantom is from 1 to 50 mm thick.

Also described herein is a method of making the phantom for fibrous tissue as disclosed herein, the method including providing about 30 to 90 wt % of water, adding sodium alginate to the water, adding acrylamide to the homogenous solution, wherein the sodium alginate and the acrylamide, in combination, are about 10 to 70 wt % of the precursor solution, and wherein the ratio between the acrylamide and the alginate is 60:40 to 99:1 w/w to form a precursor solution, stirring the precursor solution, degassing the precursor solution, curing the precursor solution to form a gel. and soaking the gel in a crosslinking solution.

In some embodiments, the crosslinking solution has a concentration of at least 0.1-1M. In some embodiments, the crosslinking solution comprises calcium sulfate dihydrate.

In some embodiments, the method further includes sonicating the water and sodium alginate to assist with dissolving the sodium alginate.

In some embodiments, sonicating the solution comprises sonicating the sample for 60 seconds for every 2-3 minutes of mixing. In some embodiments, degassing the homogenous solution comprises degassing the homogenous solution in a degassing chamber for 15 minutes to 1 hour at 20-28 in Hg vacuum. In some embodiments, curing comprises curing the homogenous solution at 40-60° C. for 15 minutes to 3 hours. In some embodiments, soaking the gel in a crosslinking solution comprises submerging the gel for 6 minutes to 282 hours.

Also disclosed herein is a method of evaluating a treatment using the phantom described herein. In some embodiments, the treatment is selected from ultrasound therapy, histotripsy, shear wave elastography diagnostics, imaging, laser radiation therapy, focus laser therapy, IR/NIR laser therapy, exomer UV therapy, or RF or microwave ablation.

Tissue-mimicking gels provide a cost-effective medium to optimize histotripsy treatment parameters with immediate feedback. Agarose and polyacrylamide gels are often used to evaluate treatment outcomes as they mimic the acoustic properties and stiffnesses of a variety of soft tissues, but they do not exhibit high toughness, a characteristic of fibrous connective tissue. To mimic pathologic fibrous tissue found in benign prostate hyperplasia (BPH) and other diseases that are potentially treatable with histotripsy, an optically transparent hydrogel with high toughness was developed that is a hybrid of polyacrylamide and alginate. The stiffnesses was established using shear wave elastography (SWE) and indentometry techniques and were found to be representative of human BPH prostate tissue. Different phantom compositions and excised ex-vivo BPH tissue samples were treated with a 700 kHz histotripsy transducer at different pulse repetition frequencies (PRF). Post treatment, the hybrid gels and the tissue samples showed differential reduction in stiffness as measured by SWE. On B-Mode ultrasound, partially treated areas were present as hyperechoic zones and fully liquified areas as hypoechoic zones. Phase-contrast microscopy of the gel samples showed liquefaction in regions consistent with the target lesion dimensions and correlated to findings identified in tissue sample via histology. The required dose to achieve liquefaction in the hybrid gel was similar to what has been observed in tissue and greater than agarose of comparable or higher Young's Modulus by a factor >10. These results indicate that the developed hydrogels closely mimic elasticities found in BPH prostate tissue and have a similar response to histotripsy treatment, thus making them a useful cost-effective alternative to for developing and evaluating different treatment protocols.

Hydrogels are often used as scaffolds for tissue engineering and to model extracellular matrices for biological studies. However, traditional hydrogels are limited by their poor mechanical properties and, as a result, double network hydrogel phantoms (with both covalent and ionic crosslinking) were created which have suitable elastic moduli and high mechanical strength.

Described herein is the fabrication and characterization of the mechanical and acoustic properties of a novel three-dimensional polyacrylamide/alginate phantom hydrogel that can better represent tough fibrous tissue such as that found in patients with BPH. The phantoms were compared against ex-vivo human prostate tissue from BPH patients to determine their similarity in response to histotripsy. To evaluate treatment efficacy, B-mode ultrasound was employed along with shear wave elastography (SWE), and changes in cavitation bubble dynamics as seen under high-speed camera photography. In addition, a method utilizing phase contrast microscopy was introduced to visualize damage to the phantom structure. This work establishes the feasibility of using these phantoms to evaluate the efficacy of treatment parameters in ablating fibrous tissue.

In one aspect, a phantom for fibrous tissue is disclosed. In some embodiments, the phantom is formed from a precursor solution. In some embodiments, the precursor solution includes about 30-90 wt % of water, acrylamide, and alginate. In some embodiments, the acrylamide and alginate, in combination, are about 10 to 70 wt % of the precursor solution. In some embodiments, a ratio of acrylamide to alginate is in the range of about 60:40 to about 99:1 w/w.

In some embodiments, the precursor solution further includes 0.10-0.30 wt % of ammonium persulphate (APS) based on the weight of acrylamide, 0.02-0.10 wt % N,N-methylenebisacrylamide (MBAA) based on the weight of acrylamide, and 0.10-0.50 wt % of N,N,N',N'-tetramethylethylenediamine (TEMED) based on the weight of acrylamide.

In some embodiments, the ratio of acrylamide to alginate is in the range of about 80:20 to 95:5. In some embodiments, the precursor solution further comprises calcium sulfate dihydrate.

In some embodiments, the stiffness of the phantom ranges from 5-1300 kPa. In some embodiments, the density of the phantom is 1000-1200 kg/m$^3$. In some embodiments, the phantom is homogenous. In some embodiments, the phantom is optically transparent. In some embodiments, the phantom is from 1 to 50 mm thick.

In some embodiments, the fibrous tissue is selected from connective tissue, prostatic tissue, uterine fibroids, fibrous tumors, blood clots, vascular plaques, cirrhosis of the liver, cirrhosis tumors, organ scars and adhesions, cystic and abscess capsular tissue, skin, uterine fibroids, fibroadenomas, scar tissue, or ureteral structures.

In another aspect, a method of making the phantom for fibrous tissue as described herein, is disclosed. In some embodiments, the method includes providing about 30 to 90 wt % of water, adding sodium alginate to the water, and adding acrylamide to the homogenous solution. In some embodiments, the sodium alginate and the acrylamide, in combination, are about 10 to 70 wt % of the precursor solution. In some embodiments, the ratio between the acrylamide and the alginate is 60:40 to 99:1 w/w to form a precursor solution.

In some embodiments, the method further includes stirring the precursor solution, degassing the precursor solution, curing the precursor solution to form a gel, and soaking the gel in a crosslinking solution.

In some embodiments, the crosslinking solution has a concentration of at least 0.1-1M. In some embodiments, the crosslinking solution comprises calcium sulfate dihydrate.

In some embodiments, the method further includes sonicating the water and sodium alginate to assist with dissolving the sodium alginate. In some embodiments, sonicating the solution includes sonicating the sample for 60 seconds for every 2-3 minutes of mixing. In some embodiments, degassing the homogenous solution includes degassing the homogenous solution in a degassing chamber for 15 minutes to 1 hour at 20-28 in Hg vacuum. In some embodiments, curing includes curing the homogenous solution at 40-60° C. for 15 minutes to 3 hours. In some embodiments, soaking the gel in a crosslinking solution includes submerging the gel for 6 minutes to 282 hours.

In yet another aspect, a method of evaluating a treatment using the phantom as described herein is disclosed. In some embodiments, the treatment is selected from ultrasound therapy, histotripsy, shear wave elastography diagnostics, imaging, laser radiation therapy, focus laser therapy, IR/NIR laser therapy, exomer UV therapy, or RF or microwave ablation.

FIG. 1 is a method for preparing a phantom, in accordance with the present technology. On the right-hand side of FIG. 1 are two views of the hybrid polyacrylamide and alginate hybrid gel (also referred to as a phantom). As is shown, the phantom has a high optical transparency.

In some embodiments, the method includes adding sodium alginate to deionized water in a beaker, as shown in process block 1. In some embodiments, the deionized water is 30 to 90 wt % of the precursor solution formed in process block 4.

In some embodiments, as described in process block 2, the mixture of deionized water and sodium alginate is sonicated. In some embodiments, the mixture is sonicated at 20% amplitude.

In process block 3, the mixture (or contents: water and sodium alginate) are stirred. In some embodiments, the contents are stirred at 60 rpm. In some embodiments, the contents are stirred with a magnetic stirrer. As shown in FIG. 1, process blocks 2 and 3 may be repeated to ensure homogeneity of the water and sodium-alginate mixture.

In process block 4, liquid acrylamide is added to the beaker to form a precursor solution. In some embodiments, the amount of liquid acrylamide and sodium alginate in combination is about 10 to 70 wt % of the precursor solution. Further, in some embodiments, water is about 30 to 90 wt % of the precursor solution. In some embodiments, process blocks 3 and 4 may be repeated to ensure the precursor solution is homogenous.

In process block 5, an MBAA and APS solution is prepared.

In process block 6, all solutions are degassed. In some embodiments, all solutions includes the MBAA and APS solution and the precursor solution. In some embodiments, all solutions are degassed a 25 in Hg.

In block 7, the MBAA and APS solution is added to the precursor solution (acylamide-alginate mixture). In some embodiments, TEMED is also added to the precursor solution. In some embodiments, the precursor solution includes 0.10-0.30 wt % of APS based on the weight of acrylamide, 0.02-0.10 wt % MBAA based on the weight of acrylamide, and 0.10-0.50 wt % of TEMED based on the weight of acrylamide.

In block 8, the precursor solution is poured into cast beakers. In some embodiments, the precursor solution is then cured at 60° C. for 3 hours.

Finally, in block 9, the cured gels are soaked in a crosslinking solution. In some embodiments, the crosslinking solution is calcium sulfate dihydrate. In some embodiments, the calcium sulfate dihydrate is 1M. In some embodiments, the cured gels are soaked for 48 hours in a sealed container.

EXAMPLES

Preparation of Polyacrylamide Alginate Gel

Described herein is a modified polyacrylamide alginate hybrid gel formulation configured to mimic pathologic tough fibrous tissues. Several gel ratios (polyacrylamide: alginate) were explored and 3 weight ratios (85:15, 90:10, 95:5 w/w) were chosen to represent different tissue stiffness (15-100 kPa) and toughness. In some embodiments, the ratio between the acrylamide and the alginate is about 60:40 to 99:1 w/w. In some embodiments, the ratio between the acrylamide and the alginate is about 80:20 to 99:1 w/w. In some embodiments, the ratio between the acrylamide and the alginate is about 85:15 to 95:5 w/w. As used herein, “about” is defined as +/−5%. The overall volume of the water in the gel was held constant at 86% by weight across all gel samples. In some embodiments, the water in the gel (also referred to as precursor solution) ranges from 30 to 90 wt % of the total precursor solution.

Liquid acrylamide (40% solution by weight) was used for preparing the phantom. The photoinitiator ammonium persulphate (APS), the covalent crosslinker N,N-methylenebisacrylamide (MBAA) and the crosslinking accelerator N,N,N',N'-tetramethylethylenediamine (TEMED) were kept at ratios of 0.0017, 0.0006, 0.0028 respectively to the weight of acrylamide. As an additional step, 10 mL of 1% by weight of MBAA and APS were prepared to safely titrate the components into the mixing beaker, due to the minute quantities required for weighing and the resolution of the balance. The weights of these 3 components were in addition to the sum total. The recipe (or precursor solution) is summarized in Table 1.

TABLE 1

Sample weight and volume measurements for preparing 200 g of 85:15 Polyacrylamide Alginate gel.

| Chemical Name | Wt % from recipe | Final Quantities |
|---|---|---|
| Deionized Water | 86% | 107.03 mL |
| Acrylamide | 11.9% | 59.5 mL |
| Alginate | 2.1% | 4.2 g |
| Sum | 100% | |
| AP | 0.17% of Acrylamide | From 1% AP - 4.046 mL |
| MBAA | 0.06% of Acrylamide | From 1% MBAA - 1.428 mL |
| TEMED | 0.28% of Acrylamide | 0.052 mL |

1M solution of $CaSO_4 \cdot 2H_2O$ is prepared by mixing 136.14 g in 1 liter of deionized water For the other gel ratios, the alginate weight was increased, and the ratio of acrylamide reduced accordingly, and the quantity of the other components adjusted. All required chemical ingredients were sourced from Sigma Aldrich Inc (St. Louis, Montana, USA).

In a fume hood, the preparation was started by adding the required volume of deionized water into a beaker. Sodium alginate was weighed using a weigh scale (PB 153-S, Mettler Toledo, Columbus, Ohio, USA) and transferred into the beaker which was then placed on a magnetic stirrer and mixed at an RPM of 300 until the alginate was completely dissolved to form a homogeneous solution. During this process, an ultrasonic processor (Vibra-Cell—VCX 500, Sonics & Materials Inc., Newtown, Connecticut, USA) was used at 25% amplitude to sonicate the sample for ~60 seconds to assist with the dissolution process for every 2-3 minutes of stirring. The required volume of acrylamide was then measured using a graduated beaker and poured into the alginate solution and stirred. The beaker was then covered with perforated aluminum foil and placed in a degassing chamber for an hour at 25 inHg vacuum. Alongside this, prepared 1% (by weight) solutions of MBAA and APS were also degassed along with an additional 500-1000 mL of deionized water. After degassing, the contents of AP, MBAA and TEMED were pipetted to the beaker and mixed using a magnetic stirrer at a low RPM of 60. The contents were transferred into multiple molding beakers to set the thickness of each gel to 20 mm and a diameter of 30 mm.

The gel was cured by UV light in a curing chamber (Form curing oven, Formlabs, Somerville Massachusetts, USA) at 60° C. for 3 hours. Post cure, the gel samples were removed from the molding beakers and thoroughly rinsed under running water to remove any residual chemicals. Further curing was performed by submerging the UV-cured gel in a crosslinking solution. Calcium sulfate dihydrate $CaSO_4 \cdot 2H_2O$, the ionic crosslinker for the alginate, was prepared by mixing the powder into degassed and deionized water. A 1M solution was chosen to ensure enough calcium ions were present for complete diffusion with extended soaking times to enable complete crosslinking.

The concentration proposed can be used for curing all the gel compositions, as it contains an excess of calcium ions. The gel phantoms were suspended in the solution for a period of 48 hours preferably in a desiccator held at 25 in Hg vacuum or in a sealed container. The time was calculated based on the Equation 1:

$$t = \left(\frac{4}{\pi}\right) \cdot \frac{H^2}{D} \quad \text{Eqn. 1}$$

where H is the half thickness of the gel, D=10^-5 cm^2 is the diffusion coefficient. Equation 1 determined the minimum time for submersion to be around 11.3 hours, however the samples were submerged for 48 hours to ensure complete diffusion. After 48 hours, the optically transparent gels were removed from the beaker, rinsed, and stored in an airtight container. Over the recorded storage period of 11 days, the maximum change in weight was found to be <7%. Storage of the gels in water is not recommended, as submergence led to swelling secondary to absorption. The summarized flowchart outlining the steps to pour the gel is shown in FIG. 1.

Two additional points are worth noting regarding the gel formulation. First, initial preparations mixed the ionic cross-linker calcium sulfate dihydrate directly into the liquid gel solution prior to UV cure, but this should be avoided as it led to a very heterogeneous gel phantom whose stiffness varied widely across the sample and made it opaque. Second, calcium chloride cannot be substituted as a crosslinker despite its high solubility and fast cross linking. Its use led to a stiff outer layer with the interior of the phantom at a lower stiffness, and also made the phantom opaque.

Preparation of Agarose Gel

Agarose gel was prepared as a 1.5% weight/volume combination of agarose and deionized water by mixing 3 g of agarose to 225 mL of water in a beaker and heated to a boiling temperature for 6 minutes. This yields a final volume equal to 200 mL which constitutes the 1.5% weight/volume gel. The gel was slowly cooled by placing it in a desiccator kept at 25 inHg to prevent any dissolution of air back into the gel, and once the mixture reached a temperature below 45° C., the contents were transferred into an acrylic container measuring 5 cm×5 cm×8 cm. When agarose was used to embed hybrid gel phantoms and tissue, the same process was followed with the addition of submerging the target within agarose during the cooling process.

Measurement of Physical and Acoustical Properties

The weights of both the polyacrylamide alginate gel and the agarose gel described herein were measured using an analytical laboratory balance and the volume using a water displacement technique in a beaker, thus yielding the density measurements. The frequency dependent attenuation and the speed of sound were measured using a through-transmission water substitution method. Once the attenuation coefficient was calculated from the fitted slope across different frequencies, the value was divided by the thickness of the gel to yield the attenuation of the sample in dB/cm/MHz.

To determine whether these samples could be used at elevated temperatures (such as boiling histotripsy), separate gel samples were vacuum sealed in food saver bags and submerged in a temperature-controlled water bath using an immersion circulator (Model No. 1112A, VWR, Randor, USA). The bath was maintained at 98° C., and the gels were kept in place for an extended period to observe if the gels remained in a solid state or melted. After the submergence period, the gels were removed from the bags, blotted, and weighed to determine if there was any significant weight loss.

Two techniques were used to estimate the stiffness (Young's modulus) of the gels, one using shear wave elastography (SWE) with an Aixplorer ultrasound platform (Supersonic Imagine, Aix-en-Provence, France) and the other using a custom-made spherical indenter setup (indentometer).

Figure 2:
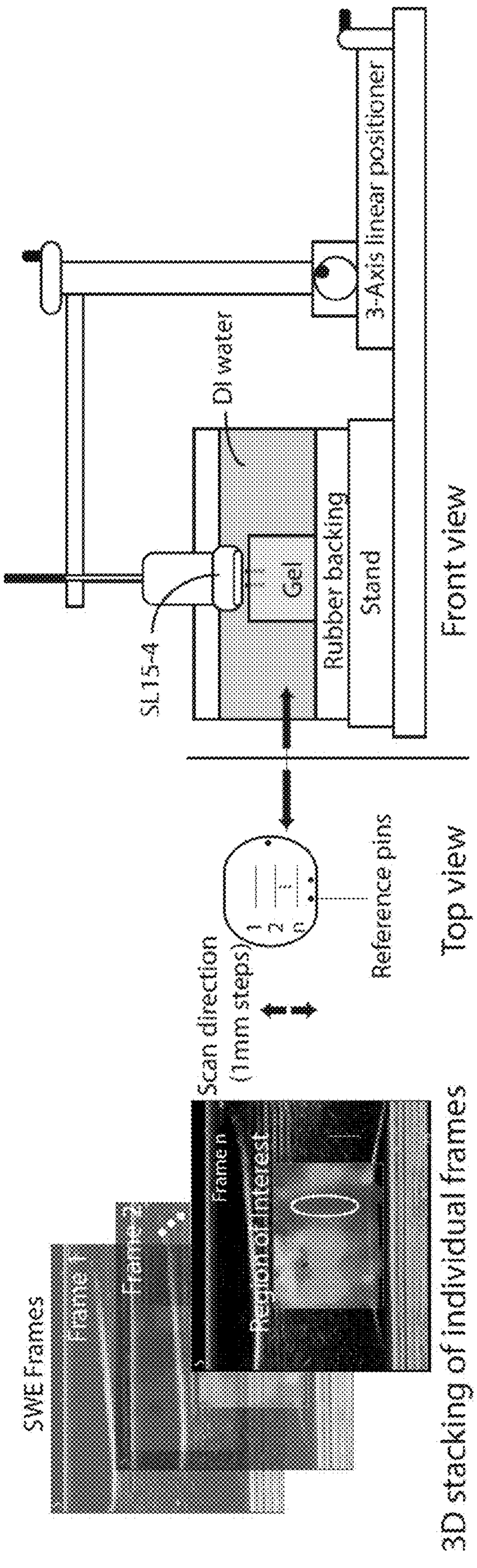
FIG. 2 is an experimental setup for testing a phantom, in accordance with the present technology.

For SWE, an SL15-4, a 256-element linear transducer (Supersonic Imagine, Aix-en-Provence, France) with a bandwidth of 4-15 MHz was mounted on to a custom built manual linear positioning system, as illustrated in FIG. 2.

FIG. 2 is an experimental setup for testing a phantom, in accordance with the present technology. A set of 16-gauge copper wires were embedded into the hybrid gels to act as locational references. Reference pins were positioned so that each remained several cm from the actual measurement zone. The gel was then placed in a container of deionized (DI) water lined with a rubber backing to absorb and reduce reverberations on a stand. Measurement zones were identified and marked at known distances away from the reference pins. Each frame (SWE frame) captured provided a 2D image with shear wave data, and regions of interest were identified. The corresponding Young's modulus was measured by averaging over a small circular area ranging from 2-5 mm in diameter and the data was recorded for each slice. A 3-dimensional SWE stiffness map was recorded by moving the positioning system in intervals of 1 mm and collectively stacking the data across all frames. The transducer setup was operated in phantom penetration mode to get the most complete B-mode image and SWE data which were subsequently recorded.

A custom indentometer was built using a spherical ball indenter (8 mm diameter) attached to a vertical linear positioning stage consisting of a linear slide drive driven by a lead screw and connected to a stepper motor. An Arduino Uno microcontroller board (Arduino, Somerville, MA) with a motor driver shield was used to control the displacement of the indenter via MATLAB (MathWorks., Inc, Natick, MA). The force corresponding to each displacement was measured by a laboratory balance (Acculab ALC-320-3; Sartorius Mechatronics Corp., Bohemia, NY, USA) as the change in effective weight of the gel sample. These components allowed programmatic control of displacement with a resolution of 2.5 μm along with force measurements with a resolution of 1 mg. The indenter was brought into contact with the top surface of the gel and moved down in small steps (step size—0.2 mm) with a speed of (1 step/second) while recording the weight measured by the balance vs the indenter displacement. The shear modulus p was then calculated from Equation 2:

$$F^{\left(\frac{2}{3}\right)} = \left(\frac{16\mu}{3}\right)^{\frac{2}{3}} R^{\frac{1}{3}} \cdot d, \quad \text{Eqn. 2}$$

where F is the force acting on the balance, R is the radius of the indenter, and the d is the sample displacement. The net Poisson's ratio was reported to be close to 0.5 thus, the conversion to Young's modulus was to be done by multiplying the shear modulus by a factor of 3.

The indentometer setup was calibrated using Zerdine pucks with reported Young's modulus acquired from Computerized Imaging Reference Systems, Inc (Norfolk, Virginia, USA).

Experimental Setup and Characterization of Histotripsy Exposures

An 18-element 700 kHz transducer with an aperture of 13 cm and focal distance of 11 cm was used to mimic the commercial transducer developed by HistoSonics, Inc. The transducer was designed and fabricated with a central cavity to house coaxially a M5Sc ultrasound imaging probe of a GE Vivid E9 4D ultrasound system (GE Healthcare, Chicago, USA). A custom-built class D amplifier powered by a high voltage source (TDK Lambda GENH600-1.3) with an appropriate electrical matching network was used to drive the transducer. The beamwidth of this transducer's acoustic field at −6 dB level was measured at low output level, under linear propagation conditions using a lipstick hydrophone (HGL-0085, ONDA Corporation, Sunnyvale, CA) and was 13.25 mm axially and 2.3 mm laterally. At higher output levels, the peak focal pressures produced by the transducer were recorded using a fiber-optic probe hydrophone (FOPH2000, RP Acoustics, Stuttgart, Germany). The highest output levels used in the experiment corresponded to peak positive pressure of 103 MPa, and peak negative pressure of 20 MPa. Output levels were controlled by actively modifying the input DC voltage applied to the amplifier. After submergence into a tank filled with degassed deionized water, the position of the transducer relative to the gel was controlled using a three-axis motorized positioner with linear slides driven by lead screws and stepper motors (Velmex Bislides and VXM controller, Bloomfield, New York, USA). Agarose gels or hybrid gels (embedded in agarose) were placed into the tank using a fixture with an acoustic window that introduced minimal disruption to the acoustic pressure field. The fixture location was controlled by the motorized positioner.

Treatment Parameters:

Previous work using histotripsy to treat BPH was used as a basis for parameter selection. From the prior work by utilizing the commercial system, the following pulse parameters were used: the center frequency was set to 700 kHz with a pulse repetition frequency (PRF) of 500 Hz and pulse duration of 3 cycles (hereafter referred to as High PRF settings). The dosage was established from the prior clinical study and estimated to be equivalent to a pulse count of 25000 per point. A higher dose of 50000 pulses/point was also explored under the same parameters in a subset of phantoms.

Due to the limited efficacy of the High pulse repetition frequency (PRF) parameters in producing objective improvements in the prior clinical trial, a Low PRF (10 Hz) exposure was also tested, based on studies indicating that Low PRF, long pulse duration parameters resulted in more complete ablation due to the formation of larger bubble clouds. The pulse count was determined from the dose response performed in hybrid eels as shown in Table 2.

TABLE 2

Treatment Paradigms

| Parameters | Frequency (kHz) | Pulse Repetition Frequency (Hz) | Pulse Duration (cycles) | Mean Peak Positive Pressure (MPa)* | Mean Peak Negative Pressure (MPa)* |
|---|---|---|---|---|---|
| High PRF | 700 | 500 | 3 | 54-108 | 14-20 |
| Low PRF | 700 | 10 | 20 | 95-108 | 16.6-20 |

*For dose response, volumetric treatment, and prostate tissue experiments

The alternate parameter settings will be referred to, hereafter, as Low PRF settings. These treatment parameters were tested in order to establish robust correlation of histotripsy response in hybrid gels to ex-vivo BPH tissue. The pressure levels for creating volumetric lesions in gels and prostate, as well as evaluating the dose response of the gel were determined at +10% of the pressure threshold observed by imaging for creating sustained cavitation clouds.

Hydrogel Histotripsy Response Experiments

Four sets of experiments were conducted to determine how the hydrogel phantoms compared with existing tissue phantoms and tissue, as well as their response to histotripsy sonication. These experiments are delineated below. A detailed diagram of the bench top hybrid gel experimental test and visualization (high Speed camera, LED light source, focusing lens and power source) setup is presented in FIG. 3. For treating tissues, a similar setup was used without the visualization.

i. Volumetric Treatment Experiments

The goal of these experiments was to determine the changes in the gel through B-mode imaging, SWE and visual inspection of lesion using phase contrast microscopy when creating volumetric histotripsy lesions. Phase contrast microscopy uses an optical mechanism that translates phase variations in the gel into light intensity changes that can be visualized as differences in contrast. Untreated regions have uniform, intensity, with treated regions having varying contrast.

Figure 3:
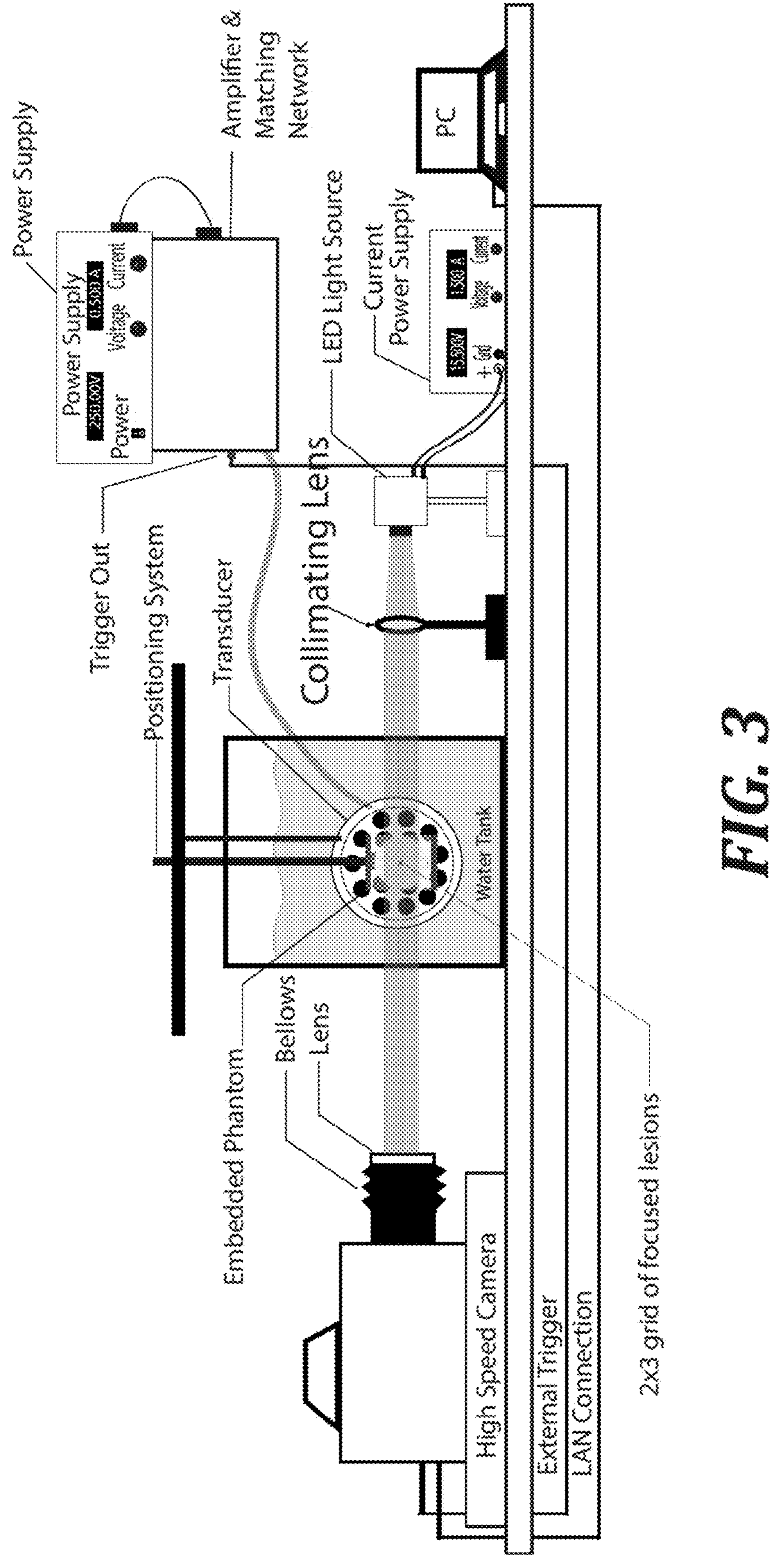
FIG. 3 is a high-speed camera setup for bubble visualization experiments in a phantom, in accordance with the present technology.

FIG. 3 is a high-speed camera setup for bubble visualization experiments in a phantom, in accordance with the present technology. The gels were sectioned and visualized using a Nikon Eclipse 80i; Nikon at 4× magnification using a phase contrast filter. A series of images were taken and stitched through NIS elements (Nikon Instruments Inc, Melville, New York, USA) to visualize the complete set of lesions and qualitatively deduce the dose response. To create volumetric lesions, gels (n=3 per type) were first mounted on a fixture and placed into a tank of degassed and deionized water as shown in FIG. 3. Volumetric treatment zones were then created by translating the gel sample with the motorized positioner in a raster fashion with 1.15 mm steps within a 3×3 rectangular grid. At each step a certain number of pulses was applied: 25K or 50K per step at the High PRF setting, and 10 k per step at the Low PRF setting. Post treatment, treatment efficacy was evaluated with B-mode US, looking for hypoechoic changes indicating complete liquefaction. For SWE, pre-treatment SWE measurements of the hybrid gels (of each formulation) were taken to establish stiffness. Post-treatment the stiffness of the gels was remeasured at the same designated sites from earlier using the SWE setup to evaluate the stiffness reduction, as would be expected from tissue treated with histotripsy. A Wilcoxon signed rank test was utilized to measure the change in stiffness in each region, before and after treatment. The statistical significance was set at $P<0.05$. The SWE and B-Mode data were analyzed over 3 frames for each sample where visual cues showed a change in B-mode and SWE. The frames were chosen such that it covered a frame at the beginning of lesion, at the middle and towards the end of the lesion, thereby including the edge cases.

ii. Prostate Tissue Experiments

The purpose of this set of experiments was to compare changes in tissue with those observed in the gel phantoms. Deidentified ex-vivo human BPH prostate tissue samples (n=3 for each test setting) acquired from simple prostatectomies were sonicated to produce volumetric liquified regions. The tissue samples ranging from 5-10 cc were embedded in 1.5% agarose gels prepared as described above and the experiments were performed within 6-8 hours of collection. B-mode and SWE measurements were taken at designated locations prior to the treatment to establish baseline stiffness. The embedded sample was placed in a water tank filled with deionized and degassed water. The sample was visualized with coaxial ultrasound imaging probe, and the transducer focus was positioned at 5 mm depth within the sample. The pressure levels for prostate tissue experiments were determined at +10% of the threshold observed for creating sustained cavitation clouds in the range included in Table 2. Using a motorized positioner, treatments were performed in a grid (ranging from 3×3 to 6×6 points) spaced in a plane orthogonal to the propagation axis of the transducer at both High PRF and Low PRF exposures with step size of 1.15 mm so the foci overlapped to create a volumetric lesion. Grid sizes were varied depending on size of respective prostate samples. A pulse count of 25K and 50K per point was used for the High PRF exposure, which translated to 14.4 and 28.8 seconds treatment per step. For the Low PRF exposure, a pulse count of 5K and 10K was used, which translated to 144 and 288 seconds per point. Post treatment, the samples were reimaged using B-mode and SWE (data collected from 3 frames) and sections of the sample containing the treated lesion were fixed in formalin for histological analysis (Masson's trichrome & Hematoxylin and eosin staining). A Wilcoxon signed rank test was utilized as done prior with the gels to measure the change in stiffness in each region, before and after treatment with the statistical significance set to P<0.05.

iii. Bubble Activity Experiments

The goal of this experiment was to compare the bubble cloud generated across different gels and treatment parameters. The following steps outline the methodology for capturing bubble cloud activity. A current controlled source coupled with a LED light was used to illuminate the path of the treatment with the help of a collimating lens. The high-speed camera (Photron Fastrax APS-RX, Photron, San Diego, California, USA) with an 80-200 mm zoom lens and bellows extension was used to capture bubble activity across different treatment paradigms. A delay of 80 μs was maintained between the input pulse sent to the transducer and the camera trigger, to enable the camera to capture the bubble cloud formed 8 μs after the wavefronts arrive at the focus. The shutter speed was set to 2 μs to capture a single frame for every pulse. The amplifier and the motorized setup were controlled via MATLAB using a custom-built program. Both the agarose and hybrid gels (all 3 formulations, n=1) were sonicated with both parameter combinations at an acoustic pressure of 20 MPa P-ve, and the bubble cloud generated was captured using the high-speed camera over 2000 frames. Captured bubble cloud data was compared qualitatively to determine differences in bubble size and cloud dynamics (whether bubbles are dissolving between pulses).

iv. Dose Response Experiments

The purpose for this set of experiments was to evaluate the dose response of the 85/15 hybrid gel to a fixed set of histotripsy parameters in comparison to 1.5% agarose gel (n=1) of comparable stiffness. From this measurement, the lesion development in the gels as a function of pulse count was evaluated at a single acoustic focal site. Pressure amplitudes were set based on the threshold for sustained cavitation clouds and operated at +20% to form a single lesion. Pressure thresholds varied across both gel formulations and exposure settings but were within the range found in Table 2. The focus of the transducer was placed approximately 5 mm beneath the surface of the gel. The pulse count was varied from 20-3000 pulses in the agarose gel and from 100-10000 pulses for the (85/15) hybrid gel.

Results i. Measurement of Physical and Acoustical Properties

To evaluate polyacrylamide/alginate gels that mimic ex-vivo human prostate tissue, the mechanical properties inherent to prostate tissue were established. Using SWE, the Young's modulus of ex-vivo human prostate specimens (n=17) was determined.

Figure 4:
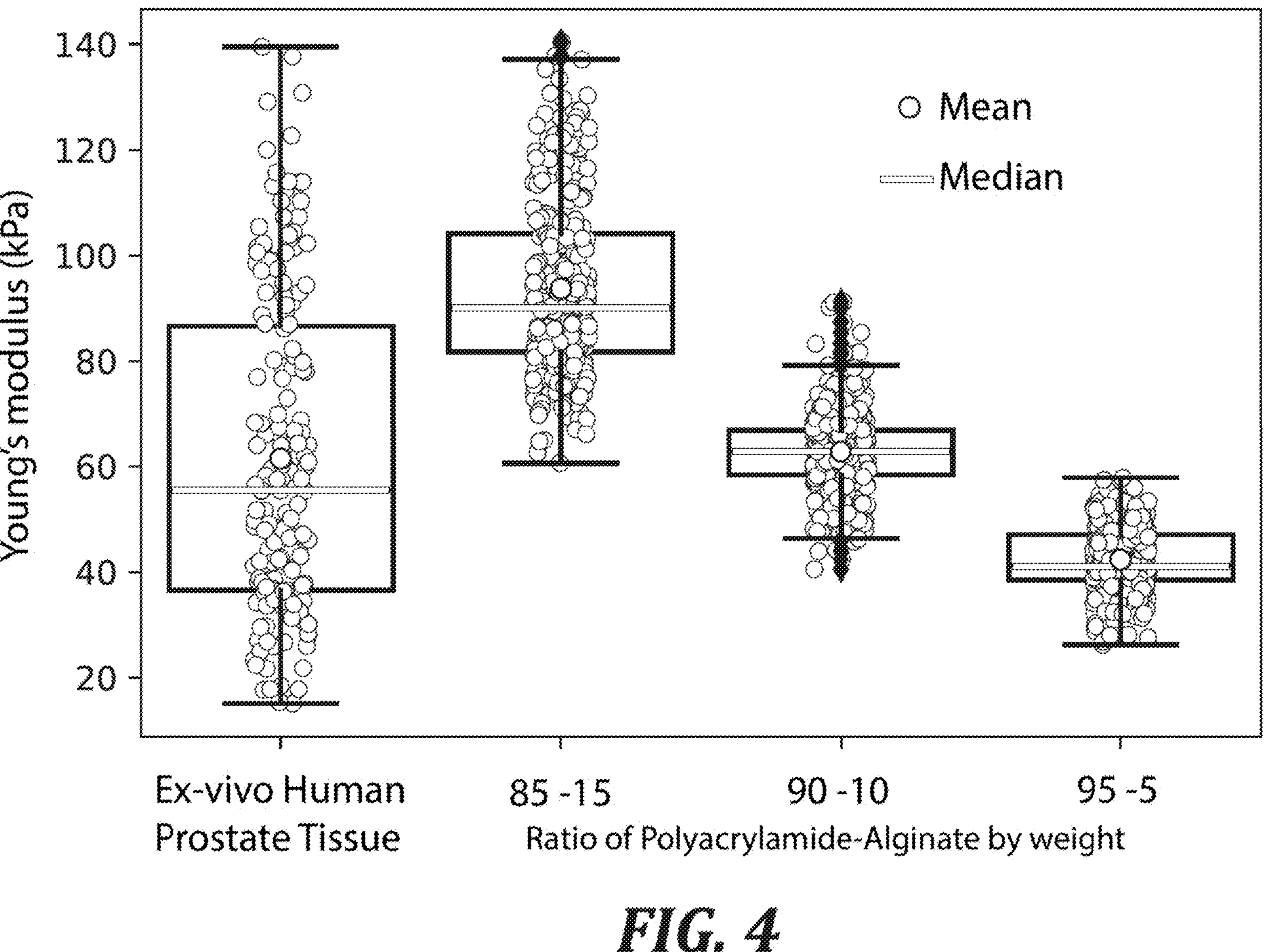
FIG. 4 is a graph showing Young's moduli for different compositions of a phantom in accordance with the present technology.

FIG. 4 is a graph showing Young's moduli for different compositions of a phantom in accordance with the present technology. On the vertical axis is the Young's modules in kPa. On the horizontal axis is ex-vivo human prostate tissue, a 85:15 ratio acrylamide to alginate phantom, a 90:10 ratio acrylamide to alginate phantom, and a 95:5 ratio acrylamide to alginate phantom.

As shown in FIG. 4, the median Young's modulus of ex-vivo human prostate tissue was 55.4 kPa with an inter-quartile range (IQR) of 36.5 kPa to 87.0 kPa. Overall, values ranged from 15.1 kPa to 124.4 kPa. The gels increased in stiffness as the ratio of alginate increased, with the stiffest gel being a ratio of 85/15 polyacrylamide to alginate by weight followed by the 90/10 and 95/05 compositions, respectively. On shear wave elastography, the gels had median Young's moduli of 90.1 (IQR 81.7-104.3), 62.7 (IQR 58.4-66.8), and 41.3 (IQR 38.5-47.11) for 85/15, 90/10 and 95/05 gels, respectively. FIG. 4 illustrates that the different gel compositions can approximate the Young's moduli of BPH tissue across its stiffness range, although do not reach the extremes. The 85/15 composition approximates stiff fibromuscular elements at the $75^{th}$ percentile of BPH tissue, the 90/10 composition approximates average stiffness BPH tissue, and the 95/05 composition approximates the soft glandular elements at the $25^{th}$ percentile. Table 3 captures the calculated mean and percent deviation of the gels and the tissue which shows the gels to be relatively homogeneous with the tissue showing more heterogeneity as expected.

TABLE 3

Mean and percent deviation of the Youngs's modulus of the hybrid gels and tissue as measured using SWE.

| Gel Type | Mean ± St. Dev. (kPa) | % Deviation |
|---|---|---|
| 85/15 | 93.73 ± 16.67 | 17.78 |
| 90/10 | 62.77 ± 7.28 | 11.6 |
| 95/5 | 42.33 ± 6.011 | 14.2 |
| EVHP | 61.44 ± 29.77 | 48.45 |

Three hybrid gels from each configuration were measured using both shear wave elastography and indentometry and the results are summarized in Table 4.

TABLE 4

Indentometry vs Shear Wave of Hybrid Gels

| Gel Type | Indentometry Measured Range (kPa) | SWE Measured Range (kPa) | % Difference from SWE |
|---|---|---|---|
| 85/15 | 48.25 ± 12.06 | 63.62 ± 21.51 | 24.15 |
| 90/10 | 25.41 ± 3.97 | 37.51 ± 8.56 | 32.25 |
| 95/5 | 7.87 ± 8.80 | 11.72 ± 0.10 | 32.81 |

Table 4 illustrates the relative difference in stiffness values as measured by indentometer vs SWE for the various compositions of the hybrid gels. In general, the indentometer reported lower stiffness values with respect to SWE across all gel compositions. Additionally, the Young's moduli of the measured agarose gels (n=3) yielded a value of 109.21 kPa±3.327, by indentometry.

The acoustic properties of the hybrid gels were in-line with other well-established hydrogels (agarose) and had values representative of prostate tissue. Table 5 highlights the acoustic properties including density, speed of sound, impedance, and attenuation.

TABLE 5

Acoustic properties of polyacrylamide/alginate hybrid gels in comparison to agarose gels and prostate

| Gel Type | Attenuation (dB/cm/MHz) | Speed of Sound (m/s) | Density (Kg/m3) | Impedance (Mrayls) |
|---|---|---|---|---|
| 85/15 | −0.06 ± 0.01 | 1528 ± 6 | 1024 ± 18 | 1.57 ± .03 |
| 90/10 | −0.07 ± 0.04 | 1514 ± 5 | 1020 ± 13 | 1.54 ± .03 |
| 95/05 | −0.14 ± 0.06 | 1520 ± 5 | 1056 ± 24 | 1.61 ± .04 |
| *Agarose | −0.04-−0.46 dB/cm | 1503-1526 m/s | | |
| *Prostate | −0.72 dB/cm/MHz | 1530 m/s | | |

*Values derived from literature on B-mode indicated an untreated region while the Y denotes treated region. In comparison, the Low PRF parameters produced defined lesions in the hybrid gels as demonstrated by B-Mode images in FIG. 5B where a hypoechoic center bordered by a hyperechoic rim is observed. These changes noted on B-mode corresponded to marked changes in the Young's moduli as evidenced by the clear changes in the SWE color map for each gel formulation.

There were small variations in acoustic properties between different gel compositions across various ratios of polyacrylamide to alginate. The values ranged from 1020-1056 kg/m$^3$, 1514-1528 m/s, 1.54-1.61 MRayls and 0.06 to 0.14 dB/cm/MHz for density, speed of sound, acoustic impedance, and attenuation, respectively.

ii. Histotripsy Response Experiments a. Volumetric Treatment Experiment

The functionality of the hydrogels as tissue phantoms for histotripsy were tested. Two primary measurements for evaluating treatment effects in the hybrid gels were captured: echogenic changes on B-mode ultrasound imaging and Young's modulus changes on SWE.

Figure 5A:
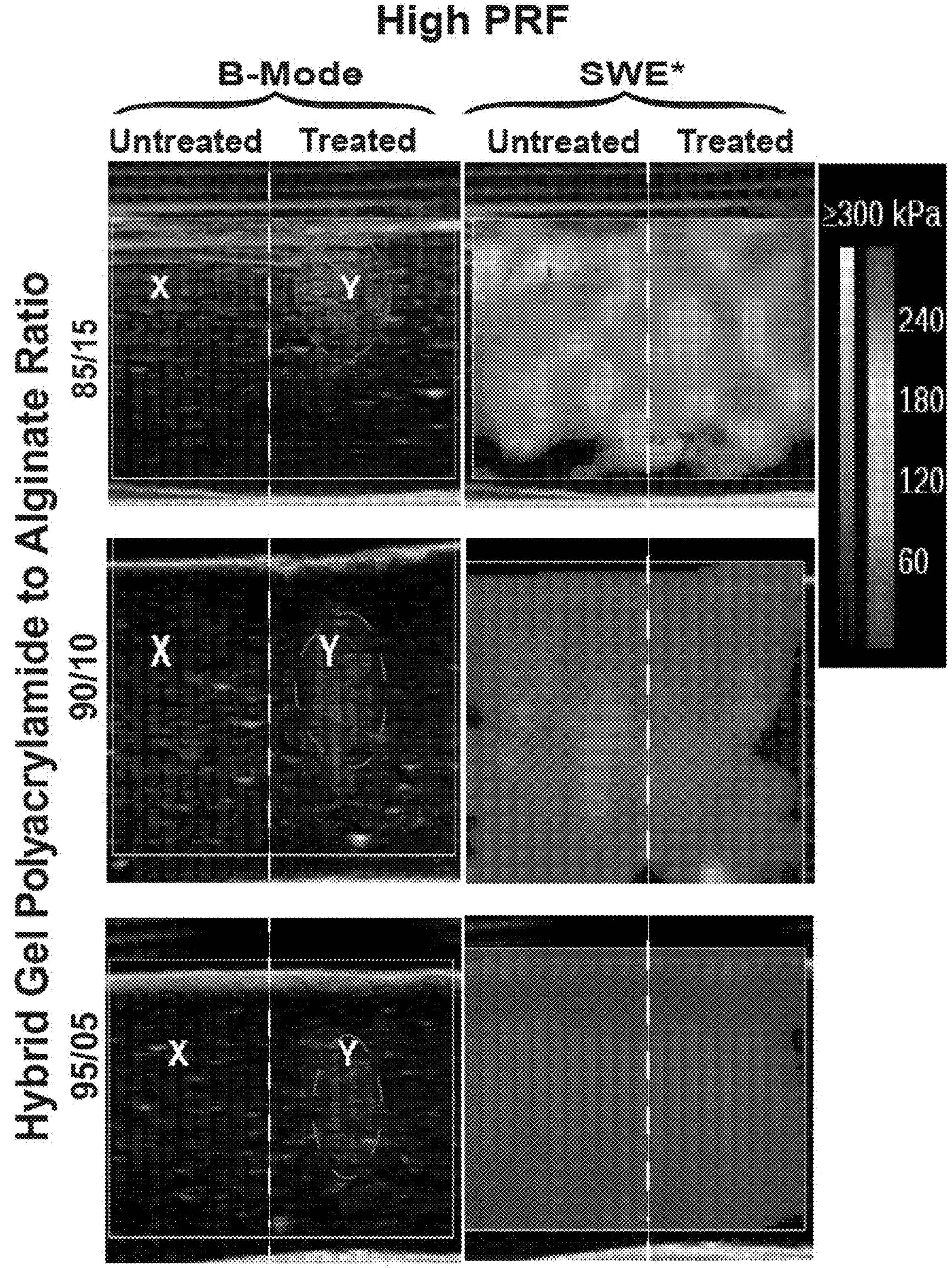
FIG. 5A shows evaluations of histotripsy with B-mode and shear wave elastography of example phantoms in high parameter settings, in accordance with the present technology.

FIG. 5A shows evaluations of histotripsy with B-mode and shear wave elastography of example phantoms in high parameter settings, in accordance with the present technology. The gels (phantoms) were a 95:5 ratio phantom, a 90:10 ratio phantom, and a 85:15 ratio phantom. On the left-hand side is the B-mode images, and on the right side is the SWE. In both test, both treated and untreated phantoms are shown. The color scale on the right-hand side shows the kPa. B-mode images in FIG. 5A demonstrate hyperechoic changes (outlined in red) in all three gel formulations treated with the High PRF exposures. However, these hyperechoic changes on B-mode did not translate to a marked difference between untreated and treated regions on the SWE color map when treated with the High PRF histotripsy parameters. B-mode and SWE evaluation of High parameter settings shows hyperechoic bubble formation on B-mode (highlighted in red) and failure of treatment to induce changes in SWE color map.

Figure 5B:
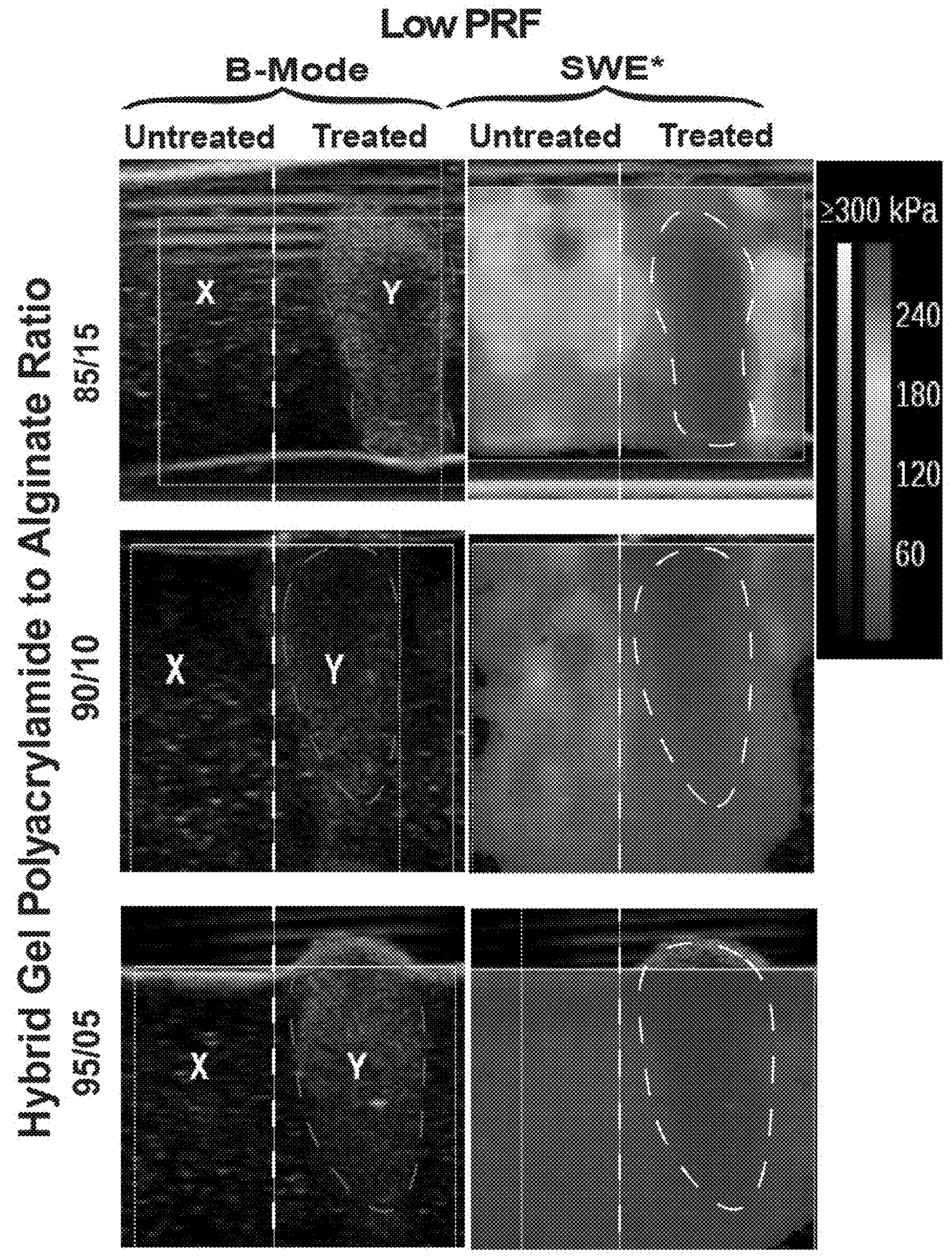
FIG. 5B shows evaluations of histotripsy with B-mode and shear wave elastography of example phantoms in low parameter settings, in accordance with the present technology.

FIG. 5B shows evaluations of histotripsy with B-mode and shear wave elastography of example phantoms in low parameter settings, in accordance with the present technology. The gels (phantoms) were a 95:5 ratio phantom, a 90:10 ratio phantom, and a 85:15 ratio phantom. On the left-hand side is the B-mode images, and on the right side is the SWE. In both test, both treated and untreated phantoms are shown. The color scale on the right-hand side shows the kPa. As is shown in FIG. 5B, B-mode and SWE evaluation of Low parameter settings showing hypo+hyperechoic changes on B-mode (highlighted in red) and corresponding distinct changes in the SWE color map (highlighter in white). The X Quantitative assessment of the change in Young's moduli is shown in Table 6, and further demonstrated the findings seen qualitatively in the SWE color map.

TABLE 6

Response of the hybrid gels and the tissue to different histotripsy parameters

| Treatment Setting | Medium | Test Statistic S Post - Pre (kPa) | P Value |
|---|---|---|---|
| | 85/15 | −13.5 | 0.129 |
| High PRF - | 90/10 | −6.5 | 0.496 |
| Low Dose | 95/05 | −22.5 | <0.005* |
| | Prostate | −15.5 | 0.0742 |
| High PRF - | 85/15 | 1.5 | 0.910 |
| High Dose | 90/10 | −5.5 | 0.5703 |
| | 95/05 | −22.5 | <0.005* |
| | Prostate | −26.0 | <0.05* |
| Low PRF | 85/15 | −20.5 | <0.005* |
| | 90/10 | −22.5 | <0.005* |
| | 95/05 | −22.5 | <0.005* |
| | Prostate | −22.5 | <0.005* |

*Statistically significant.

b. Prostate Tissue Experiment

Figure 6A:
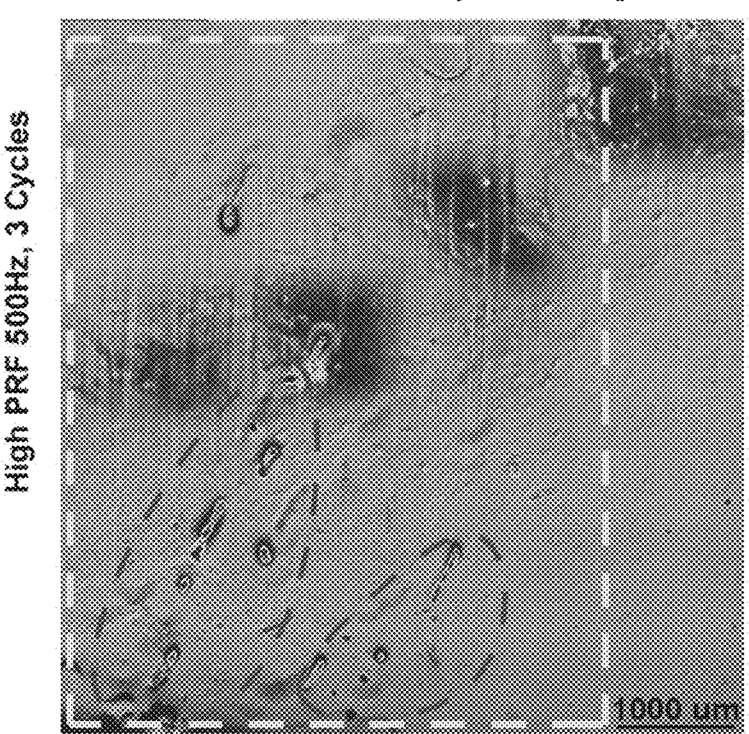
FIG. 6A shows evaluations of histotripsy induced damage under phase contrast microscopy, in accordance with the present technology.
Figure 6A:
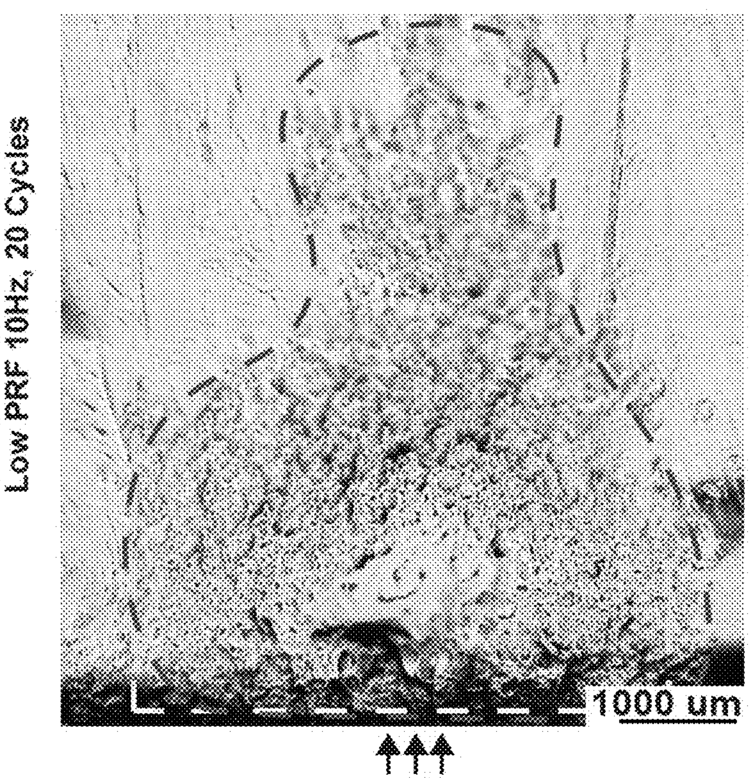
Figure 6B:
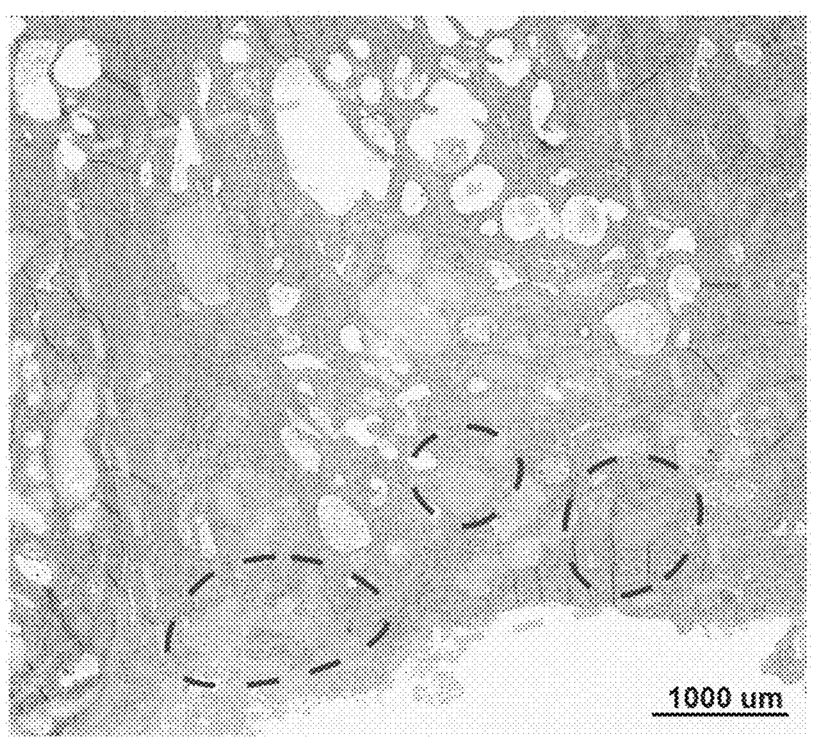
FIG. 6B is a Masson's trichrome stained ex vivo human prostate tissue; in accordance with the present technology.
Figure 6B:
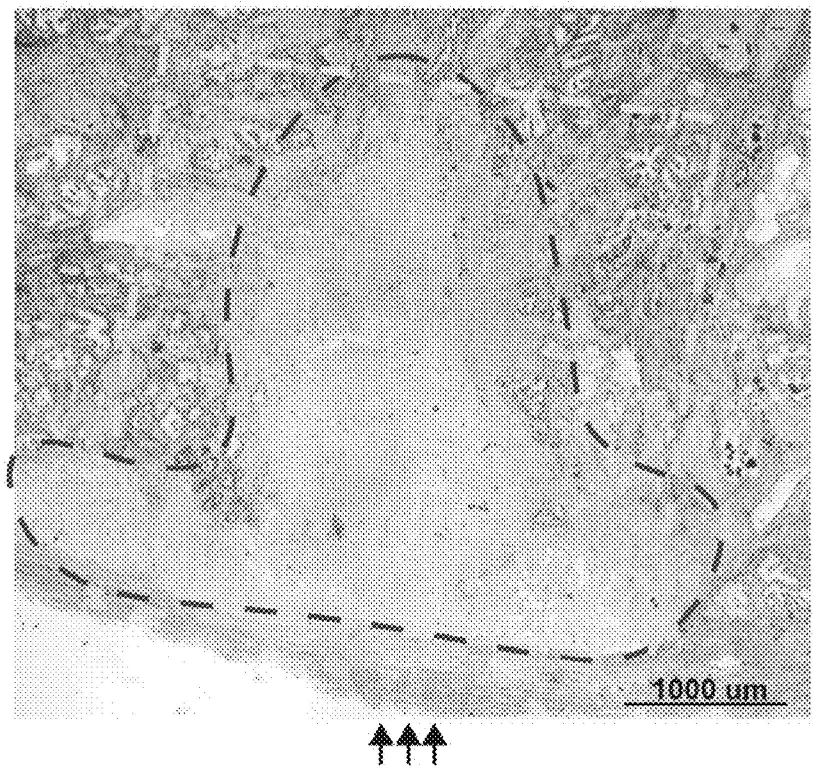

To determine the utility of hybrid gels in predicting efficacy of treatment parameters in prostate tissue samples, ex-vivo human prostatic tissue samples were treated with both High PRF and Low PRF exposures, with FIGS. 6A-6B highlighting the High PRF-High dose and Low PRF sonication for a 90-10 gel and prostate tissue of similar stiffness. Histotripsy damage was visualized under phase contrast microscopy at different parameter settings within hybrid gels and treatment effects in prostate tissue were evaluated histologically with H&E and Masson's trichome stains.

FIG. 6A shows evaluations of histotripsy induced damage under phase contrast microscopy, in accordance with the present technology. As shown in FIG. 6A, phase contrast imaging of hybrid gels at the High PRF parameter settings show sparse damage. Green outline indicated areas of histotripsy damage and yellow outline denotes area of intended/expected treatment.

FIG. 6B is a Masson's trichrome stained ex vivo human prostate tissue; in accordance with the present technology whereas for the Low PRF parameter settings it shows a higher overlap between lesions and expected area of treatment. The histologic findings (FIG. 6B) were consistent with findings seen in under phase contrast illumination for gels (FIG. 6A).

Treatment with High PRF parameters yield discrete pockets of damage rather than a contiguous homogenized lesions indicating poor concordance between treated area and expected treatment area for both the hybrid gel and the prostate tissue, covering only 19% and 12% of the expected area respectively as measured from the phase contrast image and histology section. In contrast, the treatment area generated by the Low PRF parameter settings was higher with damage seen over 72% and 66% of the expected area for the hybrid gel and tissue respectively. However, even within the treatment area, at Low PRF exposures there were some intact structures (fibromuscular stroma with glandular elements) surrounding otherwise homogenized tissue. Some visible artifacts (darkened spots) were also noted with the High PRF gel phase contrast images, that are a result of the equipment's optical limitation and the slice thickness of the sample. Quantitative assessment of the change in Young's moduli pre and post treatment for the prostate at all sonications are summarized in Table 6.

The 95/5 hybrid gel, which is lower in both stiffness and toughness among all the gels showed a significant change with $P<0.005$ in the post vs pretreatment test statistic for all treatment exposures indicating liquefaction. For the prostate, the test statistic was significant with a P value of $<0.05$ and $<0.005$ with the High PRF-High dose (50 k pulses/step) and the Low PRF exposures respectively, while no significant difference was seen with the High PRF-Low Dose (25 k pulses/step) exposure. For the 90/10 and 85/15 hybrid gel, the test statistic was significant with a P value $<0.005$ with the Low PRF sonication indicating liquefaction, while no significant change was observed for any of the High PRF Low or High dose sonications.

c. Bubble Activity Experiment

Cavitation cloud images were recorded by high-speed photography for each exposure in the hybrid and 1.5% agarose gels.

Figure 7A:
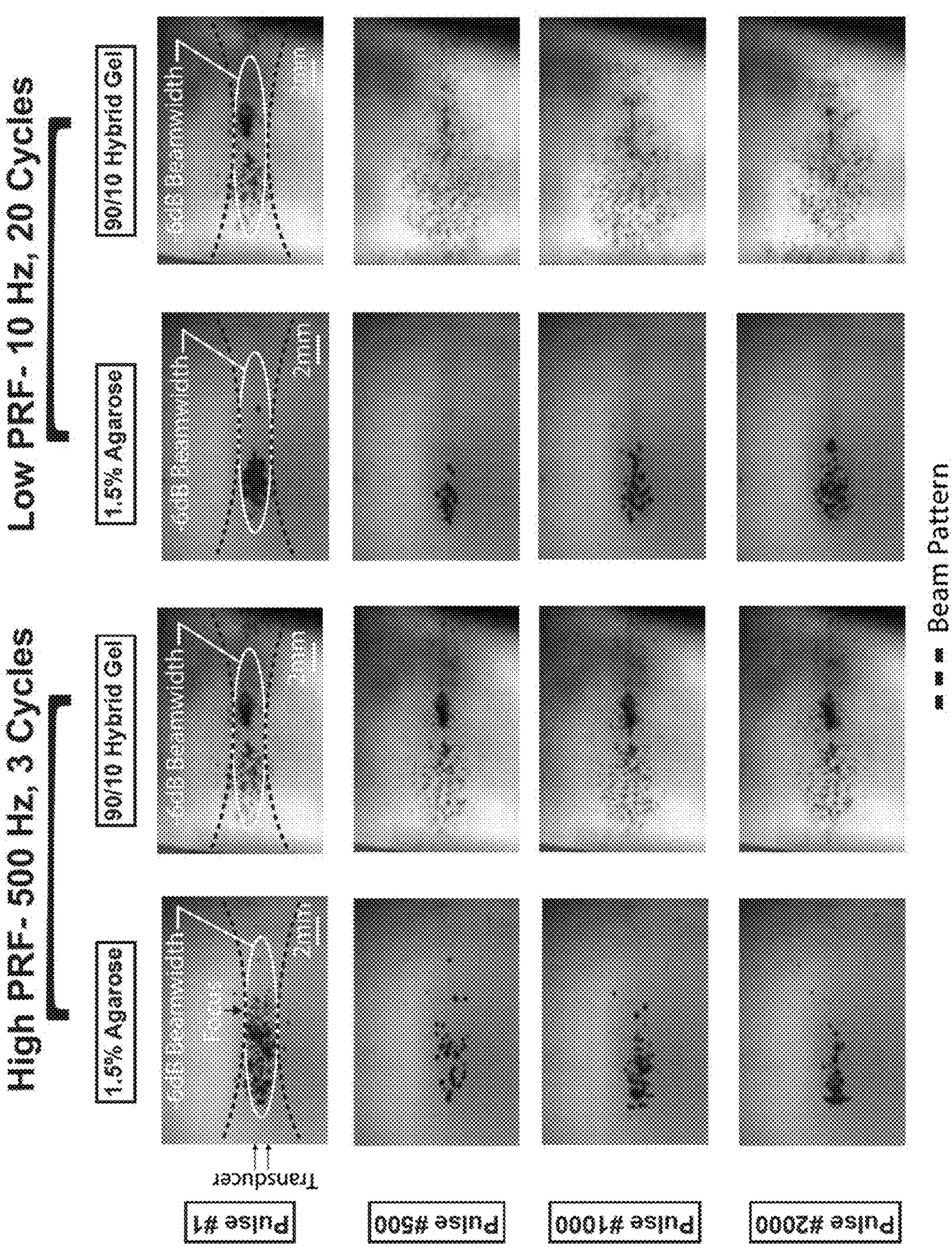
FIG. 7A shows high speed camera images showing a cavitation cloud progression in agarose and acrylamide/alginate hybrid phantoms, in accordance with the present technology.
Figure 7B:
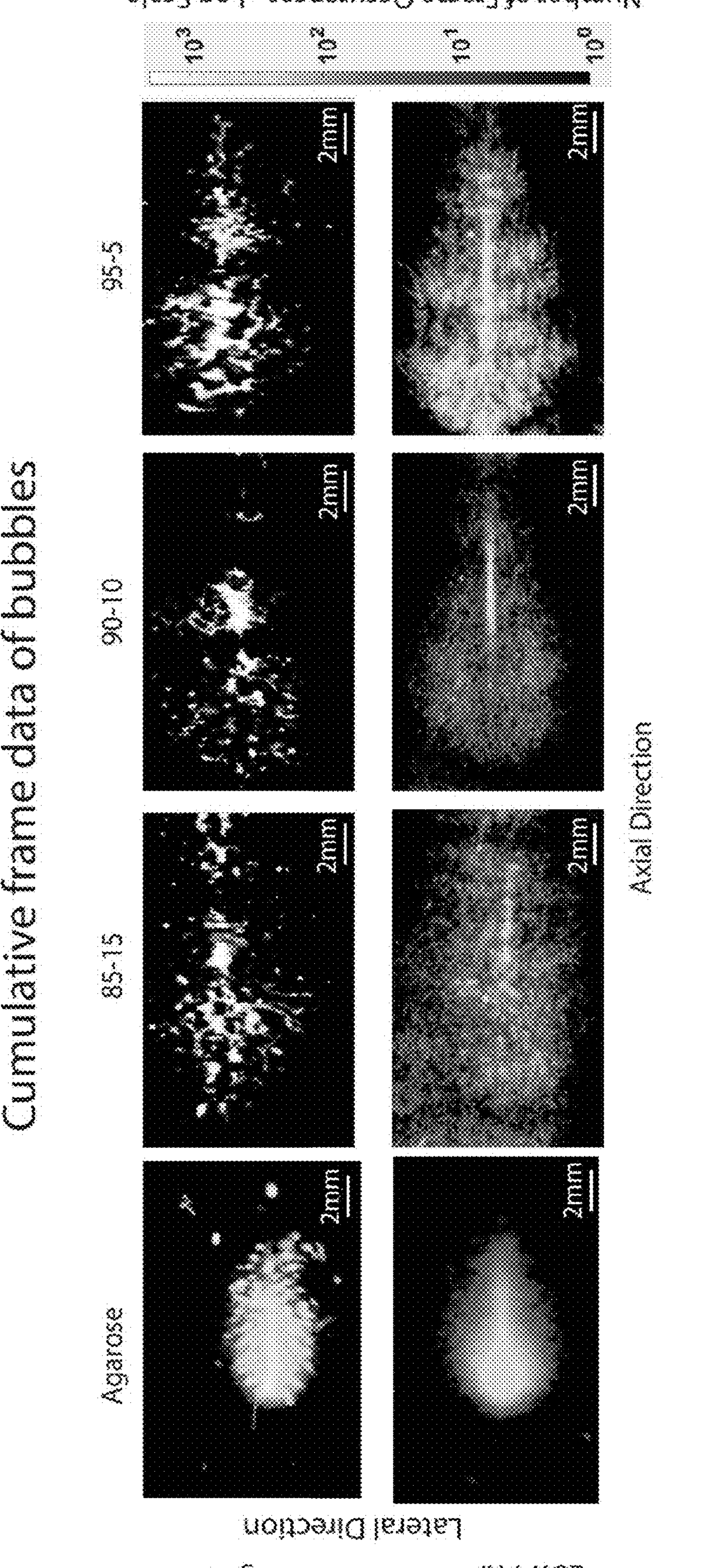
FIG. 7B shows superimposed bubble clouds from all 2000 frames of a test; in accordance with the present technology.

FIG. 7A shows high speed camera images showing a cavitation cloud progression in agarose and acrylamide/alginate hybrid phantoms, in accordance with the present technology. FIG. 7A highlights the difference in the cavitation cloud between agarose gels and hybrid gels (90/10 for example) over frames 1, 500, 1000, and 2000 while part B shows the overlay of the bubble cloud over 2000 frames. In agarose gels, irrespective of the PRF, the cloud appeared predominantly around the focus, with bubbles appearing at different locations between pulses, although appearing denser with the Low PRF. In the hybrid gels, the cloud pattern appeared static (i.e., bubbles formed in the same locations between pulses) with minimal cloud changes for the High PRF exposure, almost occurring for all 2000 frames. In contrast, when treated with the Low PRF exposure, there was an observable increase in the cloud area and formation of new bubbles in successive pulses. FIG. 7B shows superimposed bubble clouds from all 2000 frames of a test; in accordance with the present technology. The bubble area increase, as seen in FIG. 7B was also substantially greater than the agarose gel exposed to similar exposures. In FIG. 7B, the dynamic range of frames are measured varying across Low and High PRF settings, with the white arrows encompassing the total cumulative cloud observed.

d. Dose Response Experiment

Figure 8A:
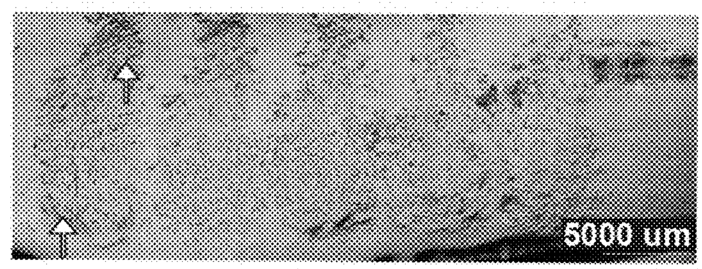
FIGS. 8A-8B show phase contrast images for Low PRF parameter settings in two example phantoms, in accordance with the present technology.
Figure 8B:
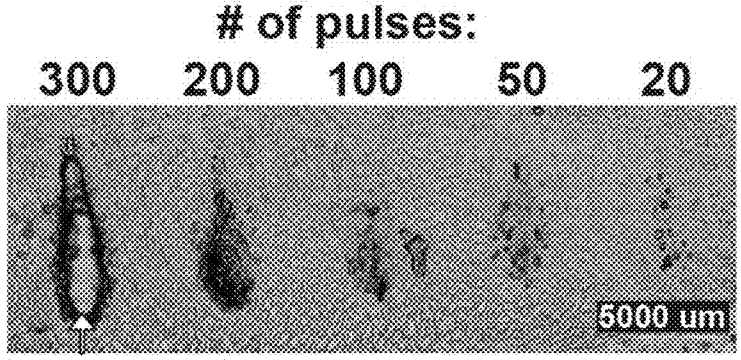

FIGS. 8A-8B show phase contrast images for Low PRF parameter settings in two example phantoms, in accordance with the present technology. FIGS. 8A-8B show the dose response to Low PRF exposures under phase contrast microscopy in an 85/15 polyacrylamide hydrogel and a 1.5% agarose gel. Both gels were treated at different doses to determine the minimal threshold to produce a liquefied cavity. As seen in FIG. 8A, the hydrogels show damage at 400 pulses and appear similar up to 3000 pulses. The damage causes optical variations within the hybrid gels, but fails to form a complete liquefactive cavity, covering only 37% of the total lesion volume. In contrast, histotripsy damage with Low PRF exposures produced prominent damage in 1.5% agarose gels at 200 pulses with complete cavity formation occurring at 300 pulses, indicating more rapid breakdown of the gel.

In FIG. 8A, an 85/15 polyacrylamide gel is pictured, showing progressive refractive changes indicating damage at increasing pulse count. The cavity present is denoted by red arrows and the liquified zone does not encompass the entirety of the foci indicating partial liquefaction.

In FIG. 8B, a dose response evaluation in 1.5% agarose gel showing cavity formation that progresses to a portion of the beamwidth at 200 pulses with complete cavity formation (fully defined lesion) at 300 pulses (red arrow) is pictured. These images show that hybrid gels of similar stiffness are more resistant to histotripsy, as evidenced by the minimal cavity formation even with 10 times the dose administered to agarose gel.

The results demonstrate that the developed phantoms produce a response to histotripsy comparable to BPH tissue and is similar in terms of acoustical and mechanical properties, making it an appropriate candidate for optimizing treatment parameters. A variety of gel phantoms were explored in the past for treatment optimization, visualization and feedback, including agarose lined with red blood cells, polyurethane, collagen, agar, and gelatin polyacrylamide. While these gels closely approximate both the acoustic and mechanical properties of soft tissue, they do not explicitly mimic the toughness of fibrous tissue. The stiffness and toughness of the current hybrid gel described in this paper could be modified by simply manipulating the ratio of acrylamide-alginate with the gels becoming highly stiff and tough as the alginate content increased. The results also further indicate that stiffness alone does not determine treatment efficacy, and that toughness is a factor, as seen in the dose response experiments (FIGS. 8A-8B) where the number of pulses required to treat the agarose was only one-tenth that of the hybrid gel of similar stiffness. The reason for the increased toughness of this phantom is the ionic cross linking of the alginate chains involving an improved ionic cross linking between calcium and carboxyl ions, which is similar to the collagen and elastin cross linking seen in fibromuscular hyperplasia typical for BPH tissue vs a weak hydrogen boding in the agarose. Fibrous tissues in general respond non-linearly to external stress, a characteristic that explains the high fracture toughness of these materials, but such materials have been treated with histotripsy effectively in the past with increased pulse count The acrylamide-alginate hybrid gel provides multiple avenues to analyze treatment efficacy. The high transparency of the gels enables study of the dynamics of cavitation through high-speed camera observations of the bubble cloud. The transparency also allowed immediate post-treatment observation of the lesion dimensions through the use of phase contrast microscopy as explored in this study. It was shown that treated regions are easily identifiable as the damage produces minor variations in the optical homogeneity of the gel, which further assists in analyzing the extent of damage.

The hybrid gels also appear to contain acoustic scatterers, thus providing a way to subject them to ultrasound imaging techniques like B-mode and SWE. B-mode imaging was successfully used in the past with RBC—agarose phantoms and bovine serum albumin (BSA)—polyacrylamide gels, where RBCs and BSA act as scatterers. SWE was shown to ascertain viscoelastic properties of the medium and as a successful imaging feedback technique in treating tissue. The hydrogels respond to histotripsy treatment in a way similar to tissue, in that fully treated volumetric lesions resolve with hypo echogenicity (white on the screen) on B-mode, with clear changes in the SWE mapping. Partially treated areas often resolved as hyperechoic zones (gray on the screen). Such features have not been observed with pure polyacrylamide and agarose gels.

The response of the gels was found to be different between sets of exposure parameters. High PRF parameters tested across the different experiments showed minimal damage both in tissue and in hybrid gels in most of the cases, whereas Low PRF parameters consistently showed significant damage. The bubble clouds observed in the gels under different parameters showed that they followed the same principles of shock wave scattering as described in previous studies. Both in High PRF and Low PRF exposures in the hybrid gels, once the sonication ended, the bubbles collapse but don't dissolve immediately, indicating a form of bubble stabilization. They were proportionally longer for the High PRF settings and with longer dose durations vs the Low PRF exposures. This could possibly be due to the structural differences between the hybrid and the agarose phantom, as such behavior was not observed on the latter. These structural differences could also explain the differences in the observed bubble cloud areas, where in the hybrid gel the bubble cloud comprised smaller bubbles spread over a larger area. In contrast, the cloud comprised larger bubbles confined to a smaller area in the agarose gel. One other possible reason for these observed differences in bubble cloud dynamics could be due to increased bubble nuclei present in hybrid gels which could interact with the incident acoustic field to make the gels more resistant to treatment. In this way, bubble nucleation could be a distinction between hybrid and agarose gels beyond the differences in structure and potential differences in toughness. Also, with the cumulative frame data from the high-speed camera video it was observed in the agarose gels that, though the clouds looked of similar shape in both High and Low PRF exposures, in the latter they tend to appear on lower number of frames which is due to liquefaction of the gel at very low pulse counts and thereby resulting in a sporadic formation of clouds, a behavior also seen in liquids.

There are several potential reasons for the relatively lower efficacy of High PRF exposures, such as bubble shielding or non-dissolution of bubbles between pulses. Pre-focal cavitation bubbles may prevent the acoustic energy from reaching the focus, as observed in other prior studies. The cumulative cloud data also showed the bubbles in the clouds occurring exclusively in the same location over the entire 2000 pulses, which could lead to liquefaction occurring only in those small areas, making it less effective. Additional experiments using High PRF settings at extremely high pulse counts at almost half a million did show measurable damage in the lower stiffness 95/5 gel, but such a dose would be impractical to perform in clinical scenarios.

The trends observed with the pre vs post treatment stiffness shear wave data for the hybrid gels and tissue are consistent with expectations that Low PRF exposures effectively liquefies them, with the statistical analysis also showing a significant change. While no such significance is seen for any gel combination or the prostate with the High PRF Low dose settings. At a higher dose however, the prostate and the less stiff and less tough 95/5 gel showed a significant change in stiffness post treatment. The reason for choosing a Wilcoxon signed rank test was due to presence of right censored data observed with some of the shear wave measurements. It is also to be noted that artifacts such as shear wave data saturation can occur in extremely small samples or when the measurements are obtained with the sample embedded in agarose.

For agarose phantoms, the use of indentometry was the only source of stiffness measurements. The indentometry technique could not measure the stiffness of the prostate samples due to their small dimensions. There was a consistent discrepancy between the shear wave and indentometry techniques measuring 24-33% lower for indentometry vs. SWE, which may be due to differences in the shear rates applied in each technique. Another limitation of the study was that the toughness of the hybrid gels and tissue samples were not directly measured. However, the toughness of similar hydrogels is reported in literature, and were further established through the dose response studies here.

This phantom may have multiple uses in the development of histotripsy therapies. For one, this gel could be expanded to test boiling histotripsy modalities, as preliminary experiments showed that these gels would not melt up near 100° C. The 3-dimensional nature and transparency of the gel also makes it easy to study the boiling bubble behavior under different exposures and provide further insights. The hydrogel described herein could further be used in a variety of histotripsy pulsing parameters, or complex treatment methodologies to reduce treatment time while maintaining efficacy.

This work demonstrated the formulation and use of a tough hydrogel from alginate-acrylamide that is optically transparent was found to mimic pathologic BPH tissue acoustic and mechanical properties. The phantoms had a response to histotripsy that could be measured by B-Mode ultrasound and SWE. The results further established that the hybrid hydrogels demonstrate similar lesion formation to actual human BPH tissue and can effectively be used to compare treatment parameters, providing immediate feedback. Such phantoms may be used in translational studies to treat BPH tissue and other fibrous tissues more effectively with histotripsy.

We claim:

1. A phantom for fibrous tissue, the phantom formed from a precursor solution comprising:

about 30-90 wt % of water;

acrylamide; and alginate, wherein the acrylamide and alginate, in combination, are about 10 to 70 wt % of the precursor solution, and wherein a ratio of acrylamide to alginate is in the range of about 60:40 to about 99:1 w/w.

2. The phantom of claim 1, wherein the precursor solution further comprises:

0.10-0.30 wt % of ammonium persulphate (APS) based on the weight of acrylamide;

0.02-0.10 wt % N,N-methylenebisacrylamide (MBAA) based on the weight of acrylamide; and 0.10-0.50 wt % of N,N,N',N'-tetramethylethylenediamine (TEMED) based on the weight of acrylamide.

3. The phantom of claim 1, wherein the ratio of acrylamide to alginate is in the range of about 80:20 to 95:5.

4. The phantom of claim 1, wherein the precursor solution further comprises calcium sulfate dihydrate.

5. The phantom of claim 1, wherein the stiffness of the phantom ranges from 5-1300 kPa.

6. The phantom of claim 1, wherein the density of the phantom is 1000-1200 kg/m$^3$.

7. The phantom of claim 1, wherein the phantom is homogenous.

8. The phantom of claim 1, wherein the fibrous tissue is selected from connective tissue, prostatic tissue, uterine fibroids, fibrous tumors, blood clots, vascular plaques, cirrhosis of the liver, cirrhosis tumors, organ scars and adhesions, cystic and abscess capsular tissue, skin, uterine fibroids, fibroadenomas, scar tissue, or ureteral structures.

9. The phantom of claim 1, wherein the phantom is optically transparent.

10. The phantom of claim 1, wherein the phantom is from 1 to 50 mm thick.

11. A method of making the phantom for fibrous tissue of claim 1, the method comprising:

providing about 30 to 90 wt % of water;

adding sodium alginate to the water;

adding acrylamide to the homogenous solution, wherein the sodium alginate and the acrylamide, in combination, are about 10 to 70 wt % of the precursor solution, and wherein the ratio between the acrylamide and the alginate is 60:40 to 99:1 w/w to form a precursor solution;

stirring the precursor solution;

degassing the precursor solution;

curing the precursor solution to form a gel; and soaking the gel in a crosslinking solution.

12. The method of claim 11, wherein the crosslinking solution has a concentration of at least 0.1-1M.

13. The method of claim 11, wherein the crosslinking solution comprises calcium sulfate dihydrate.

14. The method of claim 11, wherein the method further includes sonicating the water and sodium alginate to assist with dissolving the sodium alginate.

15. The method of claim 14, wherein sonicating the solution comprises sonicating the sample for 60 seconds for every 2-3 minutes of mixing.

16. The method of claim 11, wherein degassing the homogenous solution comprises degassing the homogenous solution in a degassing chamber for 15 minutes to 1 hour at 20-28 in Hg vacuum.

17. The method of claim 11, wherein curing comprises curing the homogenous solution at 40-60° C. for 15 minutes to 3 hours.

18. The method of claim 11, wherein soaking the gel in a crosslinking solution comprises submerging the gel for 6 minutes to 282 hours.

19. A method of evaluating a treatment using the phantom of claim 1, the method comprising:

applying the treatment to the phantom; and visualizing, after applying the treatment, the phantom.

20. The method of claim 19, wherein the treatment is selected from ultrasound therapy, histotripsy, shear wave elastography diagnostics, imaging, laser radiation therapy, focus laser therapy, IR/NIR laser therapy, exomer UV therapy, or RF or microwave ablation.

* * * * *